(12) United States Patent
McDonald et al.

(10) Patent No.: US 11,291,788 B2
(45) Date of Patent: Apr. 5, 2022

(54) GAS ADMINISTRATION MASK WITH DUAL PORT DIFFUSER AND WITH GAS REBOUND DIFFUSER

(71) Applicant: SOUTHMEDIC INCORPORATED, Barrie (CA)

(72) Inventors: Lisette McDonald, Barrie (CA); Maurice Lavimodiere, Barrie (CA); Andrew Morum, Barrie (CA); Alex McDonald, Barrie (CA); Julius Hajgato, Barrie (CA); Robert Burke, Barrie (CA)

(73) Assignee: SOUTHMEDIC INCORPORATED, Barrie (CA)

( * ) Notice: Subject to any disclaimer, the term of this patent is extended or adjusted under 35 U.S.C. 154(b) by 170 days.

(21) Appl. No.: 16/253,434

(22) Filed: Jan. 22, 2019

(65) Prior Publication Data

US 2019/0255274 A1    Aug. 22, 2019

Related U.S. Application Data

(60) Provisional application No. 62/769,418, filed on Nov. 19, 2018, provisional application No. 62/620,011, filed on Jan. 22, 2018.

(51) Int. Cl.
*A61M 16/06* (2006.01)
*A61M 16/20* (2006.01)
*A61M 16/08* (2006.01)

(52) U.S. Cl.
CPC ........ *A61M 16/06* (2013.01); *A61M 16/0816* (2013.01); *A61M 16/20* (2013.01); *A61M 2202/0208* (2013.01)

(58) Field of Classification Search
CPC .... A41D 13/0053; A42B 3/285; A61M 16/06; A61M 16/0633; A61M 16/0666; A61M 16/0672; A61M 16/0683; A61M 16/0833; A61M 16/10; A61M 16/101; A61M 16/12; A61M 16/127; A61M 2016/0661; A61M 2202/0208; A61M 2205/0216; A61M 2210/0618; A61M 2210/0625; A61M 2230/205; A61M 2230/432; A62B 18/003;

(Continued)

(56) References Cited

U.S. PATENT DOCUMENTS

| 2,560,215 A | * | 7/1951 | Christensen | ......... | A62B 18/003 |
| | | | | | 128/200.28 |
| 4,278,082 A | * | 7/1981 | Blackmer | ......... | A61M 16/0672 |
| | | | | | 128/207.18 |

(Continued)

*Primary Examiner* — Annette Dixon
(74) *Attorney, Agent, or Firm* — Pearne & Gordon LLP

(57) ABSTRACT

The invention relates to a mask for administering oxygen or other breathable gas to the nose and mouth of a patient. The invention relates to improvements in gas delivery masks, and specifically an improved diffuser structure which is particularly suitable for use in an open mask system, in which the mask body includes substantial openings that allow the user to freely converse, drink, and perform other functions. The improvements also relate to a rebound chamber within the diffuser body spaced apart from the gas conduit outlet, the rebound surface being configured to rebound and reverse the direction of flow of at least a substantial portion of the gas stream exiting the outlet from the forward direction to a rearward direction towards the user's face.

21 Claims, 42 Drawing Sheets

(58) Field of Classification Search
CPC .............. B64D 11/00; B64D 2231/025; Y10S 128/912
See application file for complete search history.

(56) References Cited

U.S. PATENT DOCUMENTS

| | | | | |
|---|---|---|---|---|
| 4,282,869 | A * | 8/1981 | Zidulka | A61M 16/0683 |
| | | | | 128/200.28 |
| 4,354,488 | A * | 10/1982 | Bartos | A61M 16/06 |
| | | | | 128/205.25 |
| 4,454,880 | A * | 6/1984 | Muto | A61M 16/06 |
| | | | | 128/205.25 |
| 5,353,605 | A * | 10/1994 | Naaman | A41D 13/0053 |
| | | | | 2/171.3 |
| 6,450,166 | B1 | 9/2002 | McDonald et al. | |
| 6,595,207 | B1 | 7/2003 | McDonald et al. | |
| 8,042,540 | B2 | 10/2011 | McDonald et al. | |
| 2006/0278232 | A1 * | 12/2006 | Nichols | A61M 16/0666 |
| | | | | 128/206.11 |
| 2012/0204872 | A1 * | 8/2012 | Cohen | A61M 16/127 |
| | | | | 128/203.12 |
| 2017/0028150 | A1 * | 2/2017 | McNulty | A61M 16/0672 |

\* cited by examiner

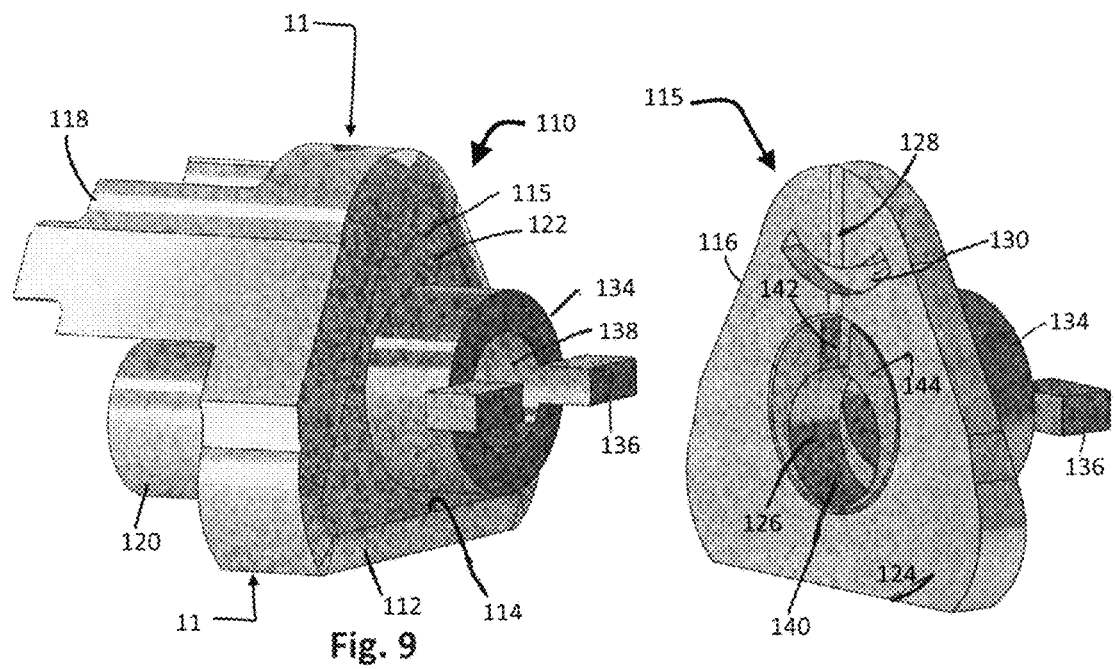
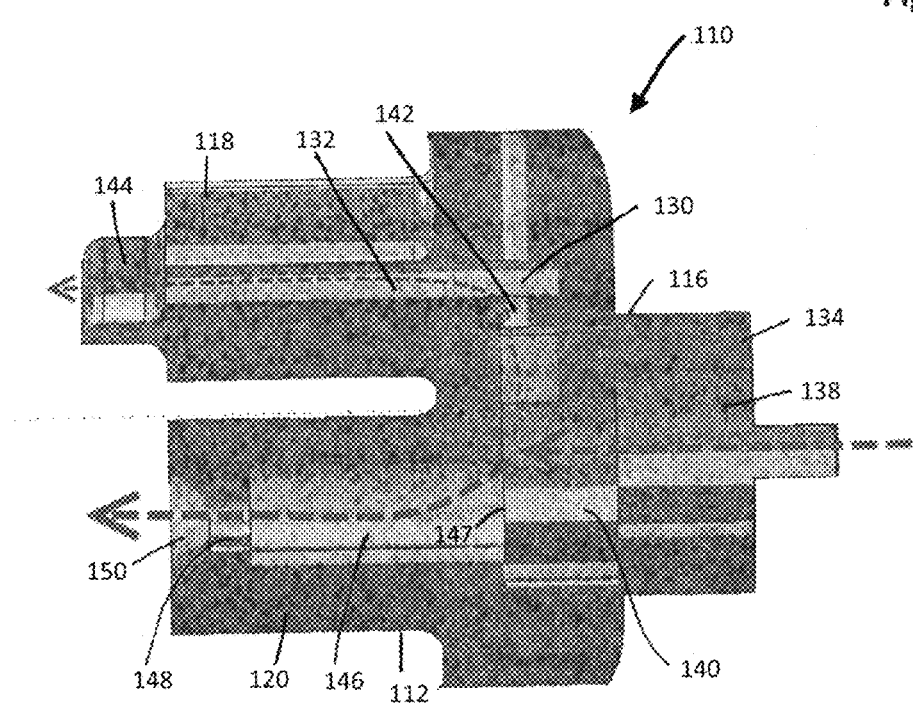

GAS ADMINISTRATION MASK WITH DUAL PORT DIFFUSER AND WITH GAS REBOUND DIFFUSER

FIELD

The invention relates to medical devices, specifically a mask for administering oxygen or other breathable gas to the nose and mouth of a patient.

BACKGROUND

Masks for the administration of oxygen and other breathable gases to a patient generally consist of a mask body which is worn over the nose and mouth region, having a soft rim for contacting the patient's face. An elastic band or other retainer holds the mask to the patient. The mask body may be fully enclosed or have substantial openings, as disclosed in previous patents listed below. An "open" mask structure has certain advantages in terms of user comfort and other benefits. An open mask allows a user to more easily converse, drink, etc. while wearing the mask.

In a typical medical mask, oxygen (or other breathable gas) is delivered into the interior of the mask through a tube, which may discharge directly into the mask or the gas flow may be obstructed by a diffuser or other structure which serves to diffuse the gas flow. In previous disclosures, a gas diffuser is provided which generates a turbulent plume surrounding the user's nose and mouth. This is useful in an "open" mask system, in order to maintain a medically sufficient gas concentration at the user's nose and mouth region, thereby reducing the amount of oxygen which escapes through the mask openings before it can be inhaled by the user. This also permits a somewhat lower gas flow rate, thereby conserving gas and increasing user comfort.

The gas velocity within such masks provides an important aspect of user comfort and the efficiency of the mask in delivering a precise level of gas concentration to a use. An overly high velocity results in user discomfort and inefficient gas delivery to the patient. However, insufficient velocity can result in an insufficient gas concentration. Precise shaping of the gas plume within the mask can assist in optimizing the gas flow rate to achieve optimal user comfort and gas concentration. This is particularly important in an "open" mask structure, which relies to a large extent on the shaping of the gas plume, rather than the mask body itself, to maintain a suitable gas concentration at the user's nose and mouth.

Gas delivery masks are also described in the following references:
U.S. Pat. No. 8,042,540 to McDonald et al.
U.S. Pat. No. 6,595,207 to Lavimodiere et al.
U.S. Pat. No. 6,450,166 to Lavimodiere et al.

SUMMARY

The present invention relates to improvements in gas delivery masks, and specifically an improved diffuser structure which is particularly suitable for use in an open mask system, in which the mask body includes substantial openings that allow the user to freely converse, drink, and perform other functions.

The mask is particularly suitable for delivery of oxygen to a patient, although it will be seen that the mask may be used or adapted to deliver other breathable gases.

We disclose a novel mask for administering a breathable gas to a patient comprising: a mask body configured to cover the nose and mouth of a patient and a diffuser mounted to the mask body for diffusing the gas rearwardly to the nose and mouth of the patient, the mask body configured to position the diffuser spaced from and opposing a nose and mouth region of the user, the diffuser comprising:
 a diffuser body;
 a bore within the diffuser body, terminating at one end in a gas inlet for connection to a gas source;
 a first gas nozzle within the diffuser body, communicating with the bore to direct a first portion of gas flow rearwardly in a first plume directed towards the user's mouth; and
 a second gas nozzle within the diffuser body, communicating with the bore to direct a second portion of gas flow rearwardly in a second plume directed towards the user's nostrils.

The first and second nozzles are configured whereby the first plume is more narrowly focused than the second plume. As well, the respective plumes (which may comprise upper and lower gas plumes) can be independently shaped and directed by the respective nozzles. For example, the first plume can have a relatively narrow spread and be directed horizontally directly towards the user's mouth, while, the second plume can have a broader spread and be deflected to angle upwardly and rearwardly towards the user's nose.

Directional references herein are used primarily for ease of description. References such as "vertical", "upright", "horizontal", etc. refer to the mask in a normal upright position, for example as used by a patient standing or sitting upright. The term "forwardly" refers to the direction away from the use's face and "rearwardly" is towards the user. It will of course be evident that the mask may be used in any orientation. Furthermore, any such directional or geometric references are not intended to be restricted to any particular degree of geometric precision, but are instead intended to include departures from such directions, as will be understood by persons skilled in the art. Furthermore, any dimensions, specifications, tolerances, etc. are intended to include departures from such values, having regard to the tolerances and other such variations and departures that would be understood by persons skilled in the relevant art, having regard to the present field of use of the invention.

We also disclose a novel mask for administering a breathable gas to a patient, comprising a mask body configured to cover the nose and mouth of a patient and a diffuser mounted to the mask body for diffusing the gas to the nose and mouth of the patient. The diffuser comprises:
 a diffuser body
 a gas conduit at least partially housed within the diffuser body and comprising an inlet for connection to a gas source and a gas conduit outlet within the interior of the diffuser body, the gas conduit outlet being configured to discharge a stream of gas into the interior of the diffuser body in a forward direction away from the user's face;
 a rebound chamber within the diffuser body having a rebound surface spaced apart from and opposed to the gas conduit outlet, the rebound surface being configured to rebound and reverse the direction of flow of at least a substantial portion of the gas stream exiting the outlet from the forward direction to a rearward direction towards the user's face; and
 at least one diffuser outlet in fluid communication with the rebound chamber for channeling the gas stream from the rebound chamber towards the user's face.

The rebound chamber optionally includes a gas flow spreader comprising a member, such as a generally dome or cone-shaped member, opposed to and projecting towards the conduit outlet and configured to spread the gas stream prior to contacting the rebound surface.

The gas rebound surface may have various configurations. In one example, the rebound surface has a curved surface around its perimeter, which is configured to redirect the gas stream in a curving path from the direction away from the user's face to the direction towards the user's face, such as a toroidal channel having a curved surface facing the gas outlet. We also disclose that the rebound surface may comprises a flat wall opposed to the outlet, for example in which the rebound surface has a frustoconical configuration.

Directional references herein are used primarily for ease of description. References such as "vertical", "upright", "horizontal", et cetera referred to the mask in a normal upright position, for example as used by a patient standing upright. The term "forwardly" refers to the direction away from the use's face and "rearwardly" is towards the user. It will of course be seen that the mask may be used in any orientation. Furthermore, any such directional references are not intended to be restricted to any particular degree of geometric precision, but are instead intended to include departures from such directions, as may be easily understood by persons skilled in the art. Furthermore, any dimensions, specifications, tolerances, et cetera are intended to include departures from such values, having regard to the tolerances and other such variations and departures that would be understood by persons skilled in the relevant art, having regard to the present field of use of the invention.

DEFINITIONS

"Oxygen" includes oxygen-enriched air. Furthermore, since the present invention is suitable for a range of breathable gasses, it will be understood that the present embodiments described herein may be used or adapted to use other such breathable gasses.

BRIEF DESCRIPTION OF THE DRAWINGS

FIG. 9 is a perspective view of a diffuser according to a further embodiment, from the front.

FIG. 10 is a perspective view of the valve assembly portion of the diffuser of FIG. 9, from the rear, showing the valve in a first position to provide a dual flow mode of operation.

FIG. 11 is a cross-sectional view thereof along line 11-11 of FIG. 9, showing internal gas flow in the dual flow mode.

DETAILED DESCRIPTION

Figure 1:
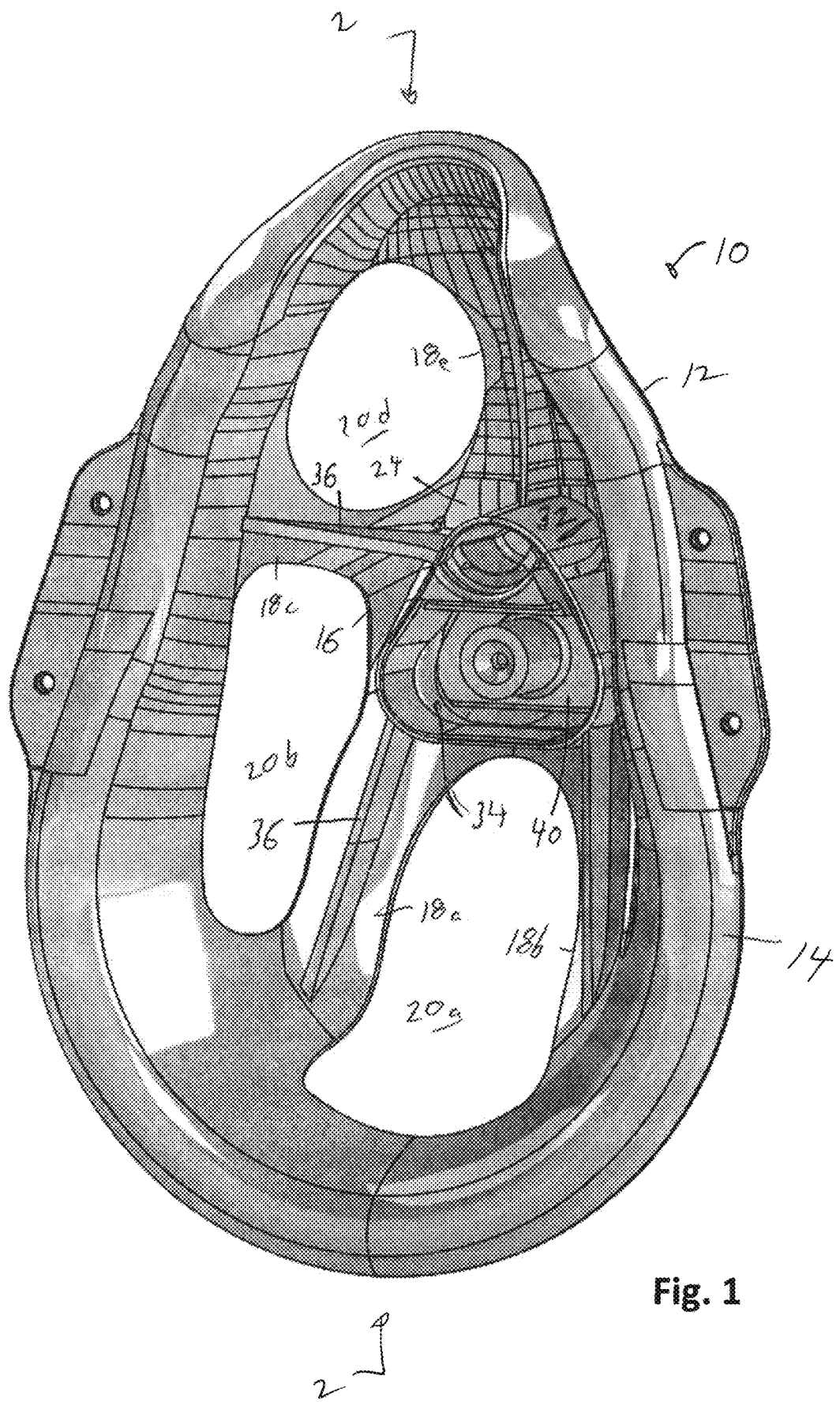
FIG. 1 is a perspective view of an oxygen delivery mask according to an embodiment of the invention.
Figure 1A:
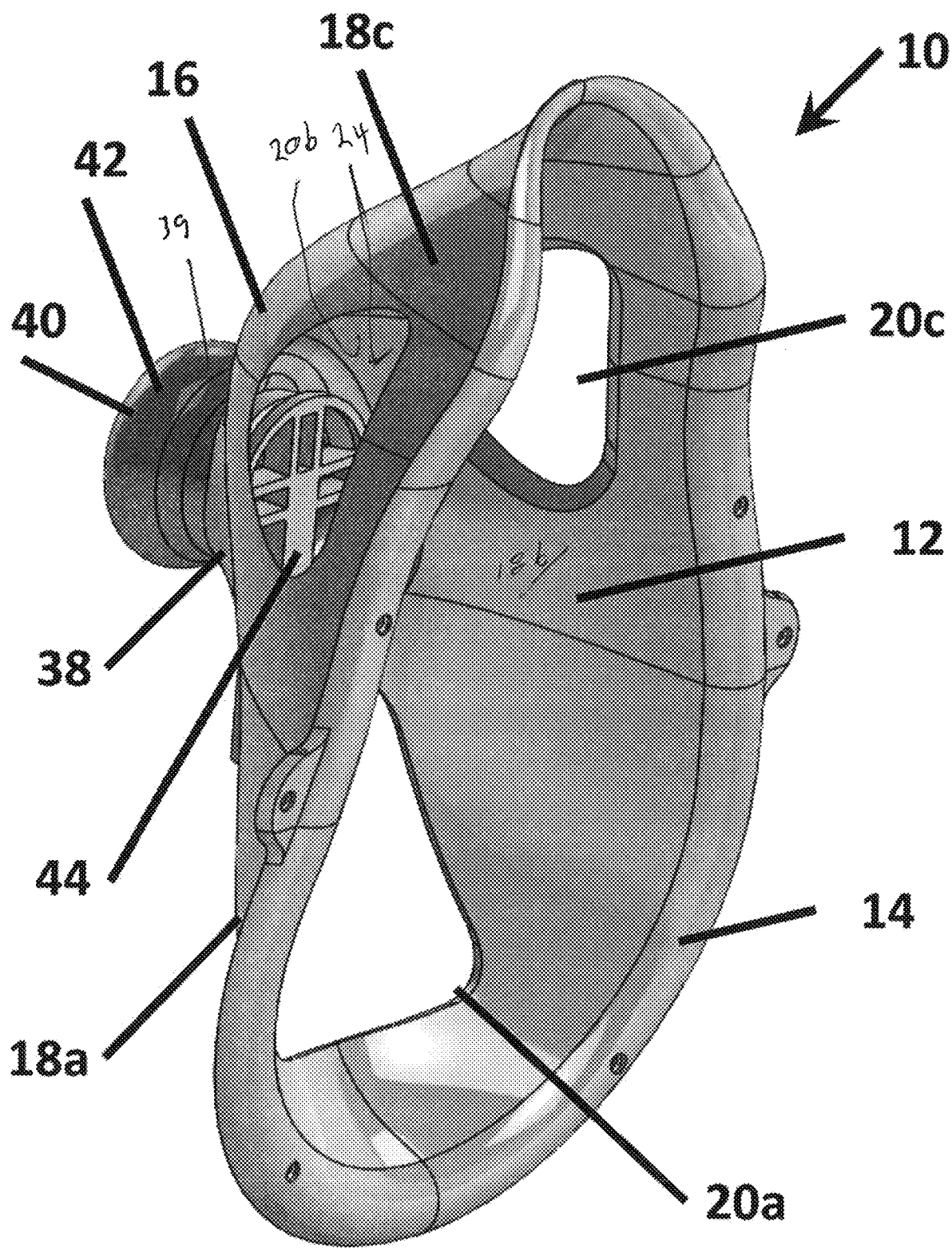
FIG. 1A is a perspective view of an oxygen delivery mask according to an embodiment of the invention.

Referring to FIGS. 1-7, a mask 10 according to a first embodiment comprises a mask body 12 which comprises a flexible molded plastic wall having a concave interior. The exposed rim 14 of mask body 12 is pliable and is configured to contact the patient's face so as to substantially surround the nose and mouth region of a typical individual. Different mask sizes may be provided to accommodate, for example, adults, children, infants etc. The mask body may be similar in configuration to the oxygen delivery masks described in U.S. Pat. No. 8,042,540 to McDonald et al., which is incorporated herein by reference. According to this aspect, mask body 12 has a generally "open" structure composed of a central hub 16 and bridges 18 collectively comprise individual portions 18a, 18b, 18c, 18d, and 18e that radiate outwardly between hub 16 and rim 14. Open areas 20 are located between bridges 18. As shown, open areas 20 collectively comprise individual areas 20a, 20b, 20c, 20d, and 20e are located between portions 18a-e and the areas of these combined may form about 30-80% of the surface area of mask body 12. Areas 20a-e individually comprise a central lower area 20a which is approximately opposed to a user's mouth, lateral areas 20b and c on opposing sides of central lower area 20a and opposing upper areas 20d and e which are on opposing sides of mask body 12 are located approximately adjacent to and on opposing sides of a user's nose bridge. Lower bridging portions 18a and b define the lateral edges of the central lower area 20a. Lower portions 18a and 18b curve rearwardly towards the user's face at their lower ends, whereby the exposed edges of mask body 12 and rim 14 that surround the central lower area 20a define a curved plane.

Mask 10 may be secured to the patient by a strap or other such means, which are not shown but are generally conventional.

Hub 16 projects forwardly from mask body 12 to form a rounded snout. The inside surface of this region defines an interior space 24 within mask body 12 opposed to the lower portion of the user's face. Within space 24, an interior wall 32 projects towards the user's face from the inside surface of hub 16. Wall 32 encircles a generally triangular region, which defines a receptacle 34 opening towards the user's face. Receptacle 34 may comprise any configuration that is suitable for retaining a central diffuser 40, described below, such as rectangular, oval etc. An array of ribs 36 radiate outwardly from wall 32 and protrude rearwardly from the inside surfaces of bridges 18. Ribs 36 serve to stiffen bridges 18, so as to retain the mask structure and integrity and also to channel the gas plume within the mask interior.

According to one aspect, mask body 12 is molded as a single monolithic structure that includes rim 14, hub 16, bridges 18, wall 32 and ribs 32. Alternatively, these components may comprise different materials or have different properties, for example by assembly from individual components or by using a multi-density molding process. For example, the respective components may comprise different densities, resilience or other properties. In one aspect, bridges 18 comprise a material that is sufficiently rigid to dispense with the need for ribs 32.

As mentioned below, hub 16 has a central opening 38 access diffuser 40 from the front of mask 10 to allow a gas supply tube (not shown) to be inserted from the front into diffuser 40.

Diffuser 40 may comprise a structurally independent, rigid plastic member that is assembled to mask body 12, or alternatively it may be co-molded with body 12. In the present embodiment, diffuser 40 comprises a structurally independent component, which is snugly retained within receptacle 34 and may be secured to wall 32 by adhesive, friction fit or other fastening means.

Diffuser 40, shown in detail in FIGS. 5-8, comprises a generally flat front face 44, an opposing rear side 46 and a sidewall 50 which is configured to fit snugly within receptacle 34. Rear side 46 of diffuser 40 comprises a recessed lower wall 54 and a rearwardly projecting upper portion 56 which is configured to form a gas flow deflector, described in more detail below. The lower surface 58 of upper portion 56 forms a flat overhanging surface that projects rearwardly over lower wall 54. For reference, a front/rear longitudinal axis "a" extends between the front and rear faces of diffuser 40 (see FIG. 5).

Figure 2:
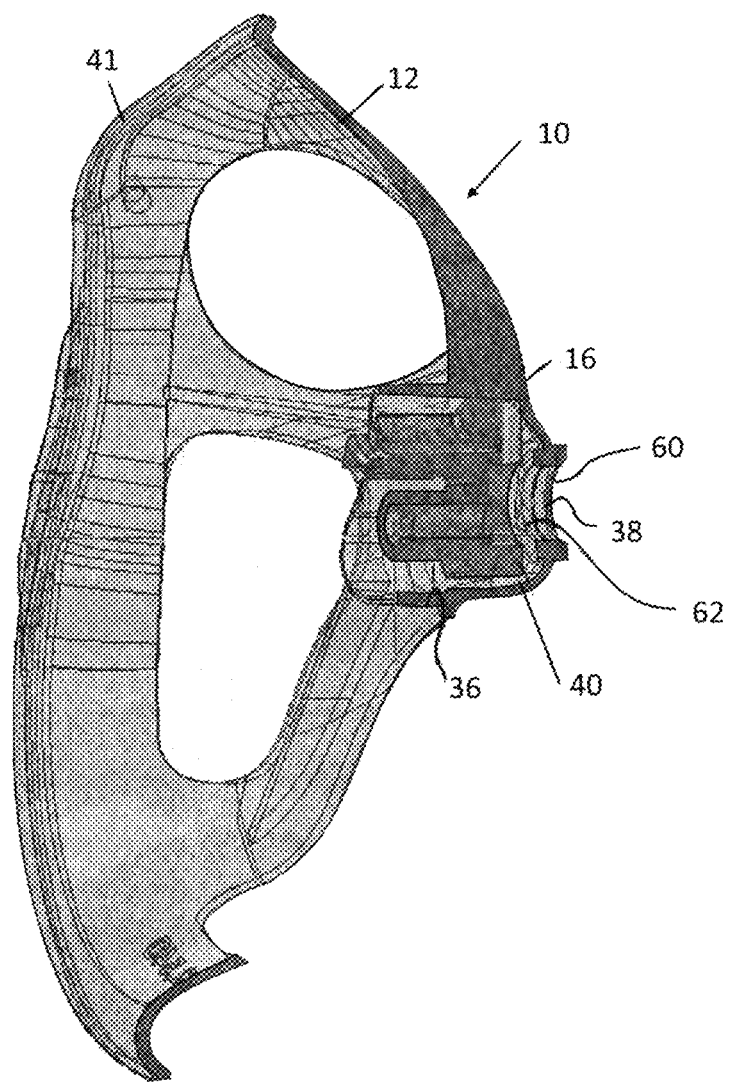
FIG. 2 is a cross-sectional view along line 2-2 of FIG. 1.
Figure 3:
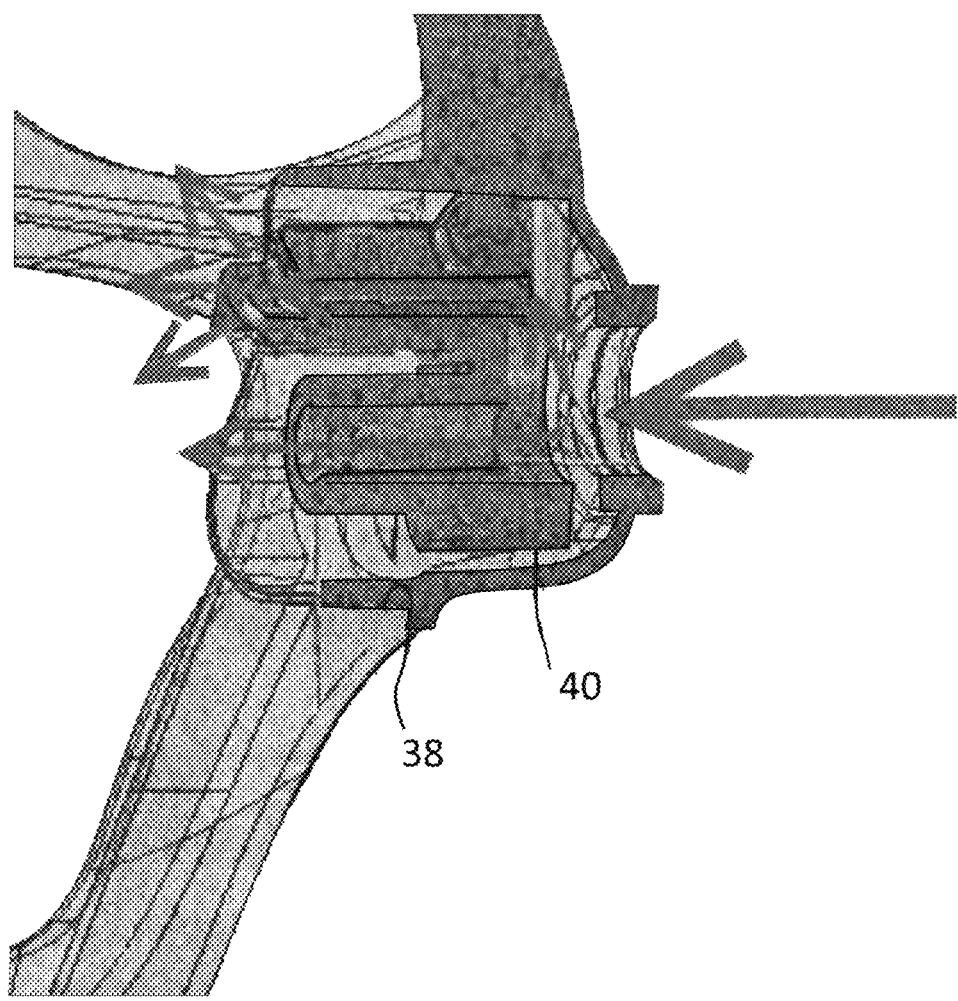
FIG. 3 is an enlarged portion of the cross section of FIG. 2.
Figure 3A:
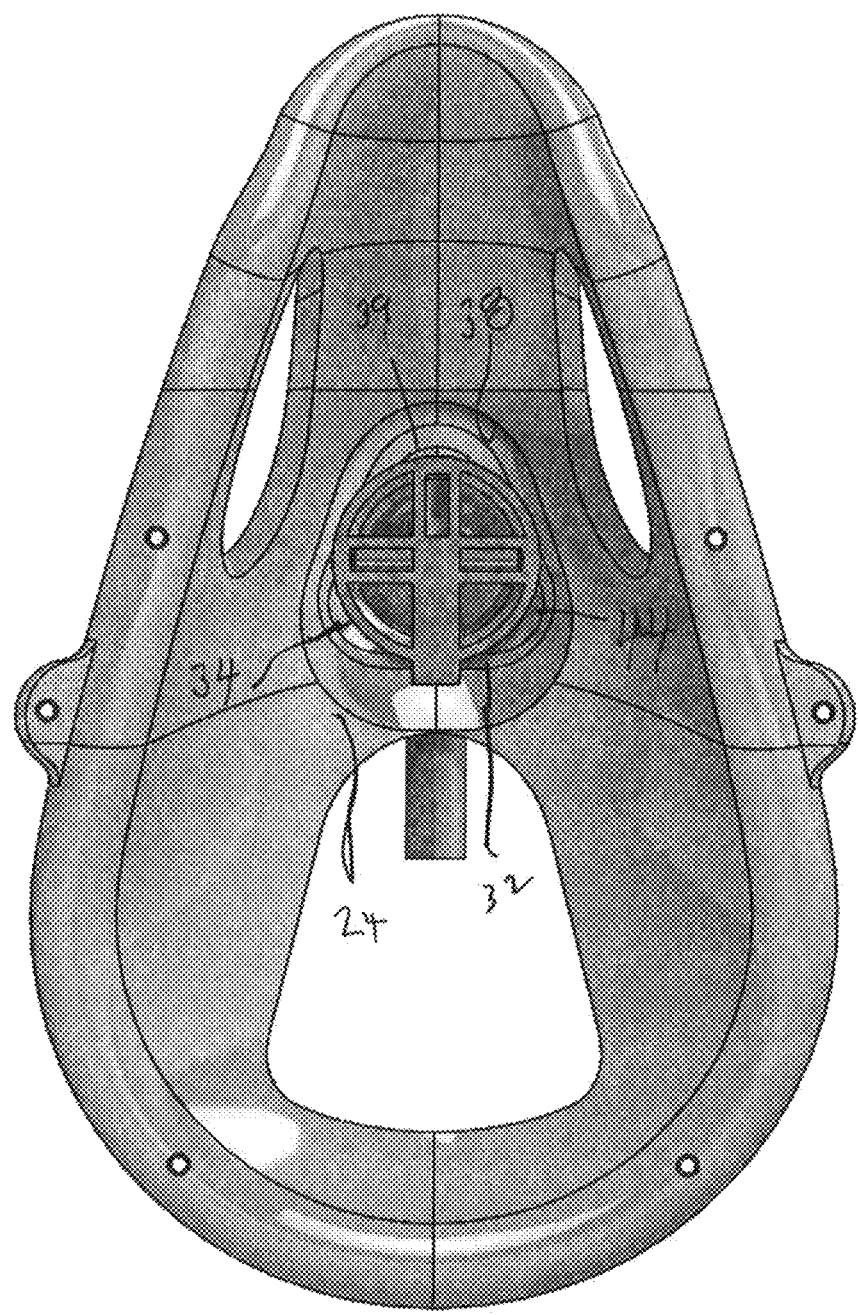
FIG. 3A is a rear view of the same, showing the interior of the mask body and diffuser.
Figure 7:
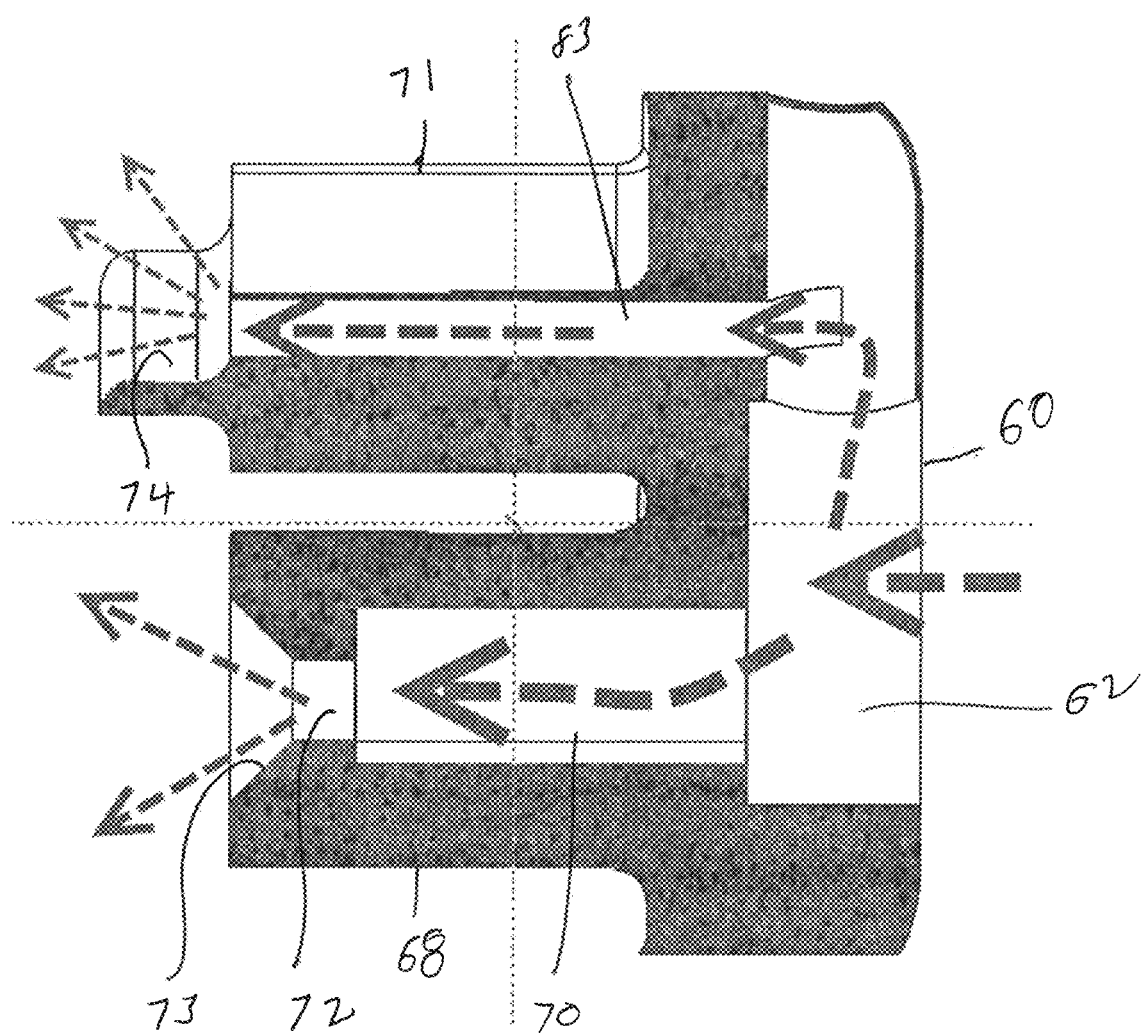
FIG. 7 is a cutaway view of the diffuser along line 7-7 of FIG. 6 showing internal structure and gas flow path.

Referring to FIGS. 2, 3 and 7, diffuser 40 has a central gas inlet port 60, located within the front face 44 of diffuser 40. Inlet port 60 is configured to receive an oxygen supply tube, not shown, leading from the source of pressurized oxygen or other breathable gas. Inlet port 60 communicates with an internal manifold 62 within diffuser 40, located adjacent to front face 44. Manifold 62 opens internally to discharge the pressurized gas through two gas discharge nozzles, consisting of a lower nozzle 68 and an upper nozzle 71.

Lower gas nozzle 68 comprises a horizontally-oriented tubular structure having an axial, horizontal internal bore 70 which communicates with gas manifold 62. Lower nozzle 68 projects rearwardly from recessed lower wall 54 towards the user's face. Lower nozzle bore 70 terminates at its outlet in a narrowed nozzle outlet 72 and a nozzle cone 73 which opens outwardly and rearwardly. Nozzle cone 73 is shaped to generate a lower gas plume 100 which is directed towards and narrowly focused on the user's mouth (see FIG. 20). As discussed below, lower gas plume 100 has a more narrow focused or spread than the upper gas plume 102 generated by the upper nozzle 71, described below. That is, the dispersion angle or spread of lower gas plume 100 is narrower than the corresponding dispersion angle of upper gas plume 102. Furthermore, the structure of lower nozzle 68 is radially symmetric about its central axis, whereby the resulting lower gas plume 100 is radially symmetric.

The upper portion of diffuser 40 comprises upper gas nozzle 71 and a gas flow deflector structure 74. Flow deflector structure 74 comprises a U-shaped trough which project rearwardly towards the users face. The elongate axis of trough 74 is aligned with front/rear axis "a" of diffuser 40. Trough 74 is stepped downwardly relative to a gas discharge slot 83. As discussed below, trough 74 is configured to direct upper gas plume 102 in a generally upward direction relative to axis "a".

Gas is discharged from upper gas nozzle 71 through an arcuate, generally horizontal slot 83 (see FIGS. 4-7) which communicates internally with manifold 62 at its forward end and opens at its rearward end towards the patient's face. Gas discharged by upper nozzle 71 forms a plume that is shaped by slot 83 and trough 74 in a generally upward direction, whereby the lower border of upper gas plume 102 is generally horizontal and its upper portion is unconfined and thus its upper border tends angle upwardly towards the user's nostrils. As such, upper gas plume 102 is asymmetric about a main horizontal axis aligned with axis "a". Furthermore, due to the relatively wide slot-shaped nozzle opening 83, upper gas plume 102 tends to have a wider focus or spread than lower gas plume 100 at most gas flow rates.

Figure 8:
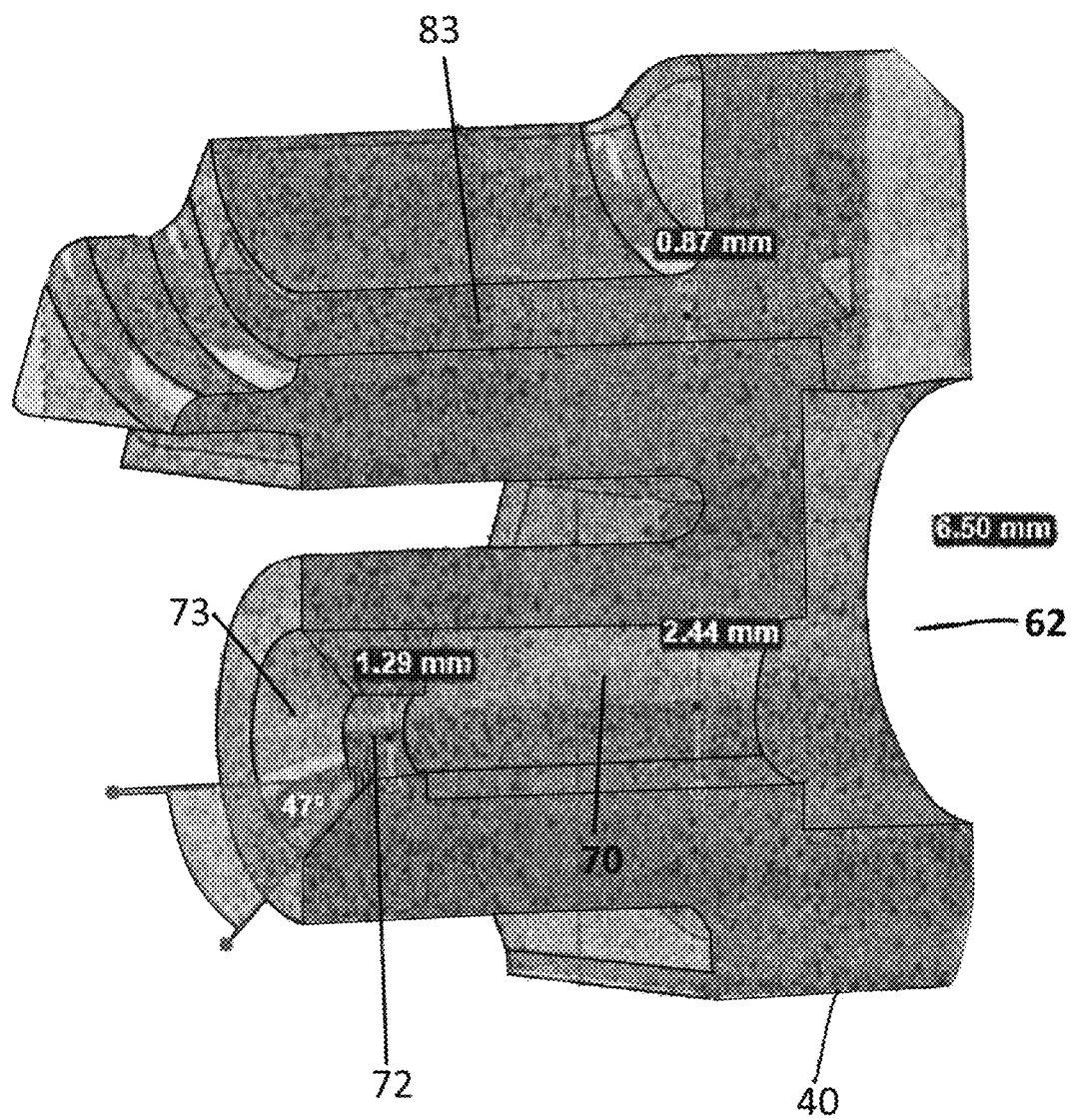
FIG. 8 is a partially cutaway view of the diffuser showing certain internal dimensions.

FIG. 8 shows dimensions of an example of the diffuser 40 of FIGS. 1-7. As seen in this Figure, manifold 70 has a top to bottom height of 6.5 mm; lower bore 62 has a diameter of 2.44 mm; lower nozzle opening 72 has an inside diameter of 1.29 mm and nozzle cone 73 has a taper of 47° from the central axis of bore 70. Arcuate upper gas discharge slot 83 has a height of 0.87 mm. These dimensions may be expressed as a ratio based on the height of manifold 62 as 100%. The diameter of lower bore 70 is 37.56% of this value; lower nozzle opening 72 is 19.79% thereof; and the height of upper slot 83 is 13.44%. According to this example, these values can vary within a range of plus or minus 5%. According other examples, these values can vary within ranges of plus or minus 10%, 20%, 30%, 40% or 50%.

FIGS. 9 to 13 show an embodiment relating to a diffuser 110 which is similar in configuration to preceding diffuser 40 and fits within a mask body in a similar fashion. Diffuser 110 comprises a diffuser body 112 having triangular recess 114 within its front face. A valve assembly comprising a valve housing 116, seen in isolation in FIGS. 10 and 12, fits within recess 114 and is configured to control airflow from an oxygen tube, not shown, to upper and lower gas nozzles 118 and 120 respectively. Valve housing 116 comprises a generally triangular plate having opposing front and rear faces 122 and 124 respectively. A circular aperture 126 extends through valve housing 116 and is open to the front and rear faces 122 and 124. A vertical groove 128 is recessed into rear face 124 and extends from aperture 126 to the top of valve housing 116. An arcuate groove 130 is recessed into rear face 124 and intersects with vertical groove 128. Groove 130 is configured to align with arcuate slot 132 within diffuser body 112.

A cylindrical valve body 134 fits within aperture 126 and is rotatable therein. Valve body 134 comprises a forwardly-projecting handle 136 that is configured to be easily gripped by a user to rotate valve body 134. Since diffuser 110 projects outwardly from the front of the mask body, handle 136 may be manipulated from outside the front of the mask by a patient or medical practitioner. Valve body 134 comprises a cylindrical front gas chamber 138, which opens to the front of diffuser 110 to receive a gas tube, not shown, and which is centered within valve body 134. Valve body 134 further comprises a cylindrical rear gas chamber 140, which is in fluid communication with front chamber 138. Rear chamber 140 is eccentrically positioned within valve body 134 whereby rotation of valve body 134 rotates the central axis of rear chamber 140. Valve body 134 further comprises a groove 142 recessed into its rear face 144. Valve body 134 is configured whereby when rear chamber 140 is rotated into its lowermost position, as seen in FIG. 10, groove 142 is vertical and is continuous with groove 128 within diffuser body 112 and in fluid communication therewith.

Upper gas nozzle 118 has a similar configuration to diffuser 40, and comprises an arcuate slot 132 which opens to a trough 144, which forms a gas deflector structure to channel the gas plume generally upwardly. Slot 132 is aligned with arcuate groove 130 within valve housing 116 whereby the respective opens form a continuous arcuate slot within diffuser 110.

Lower gas nozzle 120 is likewise similar in structure to diffuser 40 and comprises a tube having an internal bore 146 with an inlet 147 and a narrowed outlet 148. The rearmost end of nozzle 120 comprises a discharge cone 150 which channels the discharged gas into a relatively narrow plume for impacting the user's mouth.

Figure 12:
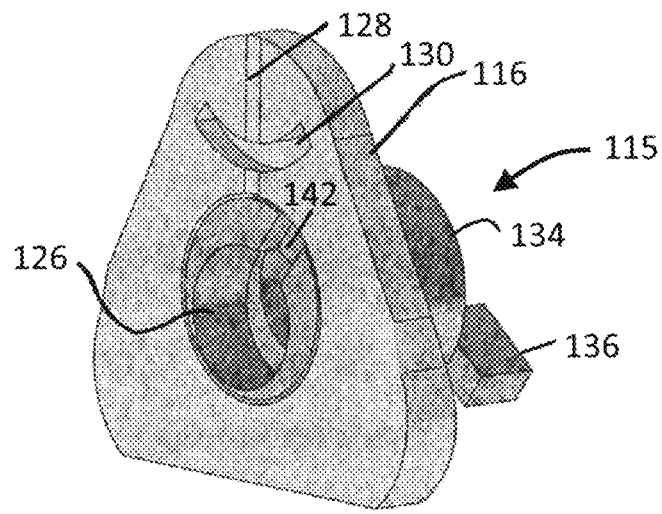
FIG. 12 is a perspective view of the valve assembly, from the rear, in a second position to provide a single flow mode of operation.
Figure 13:
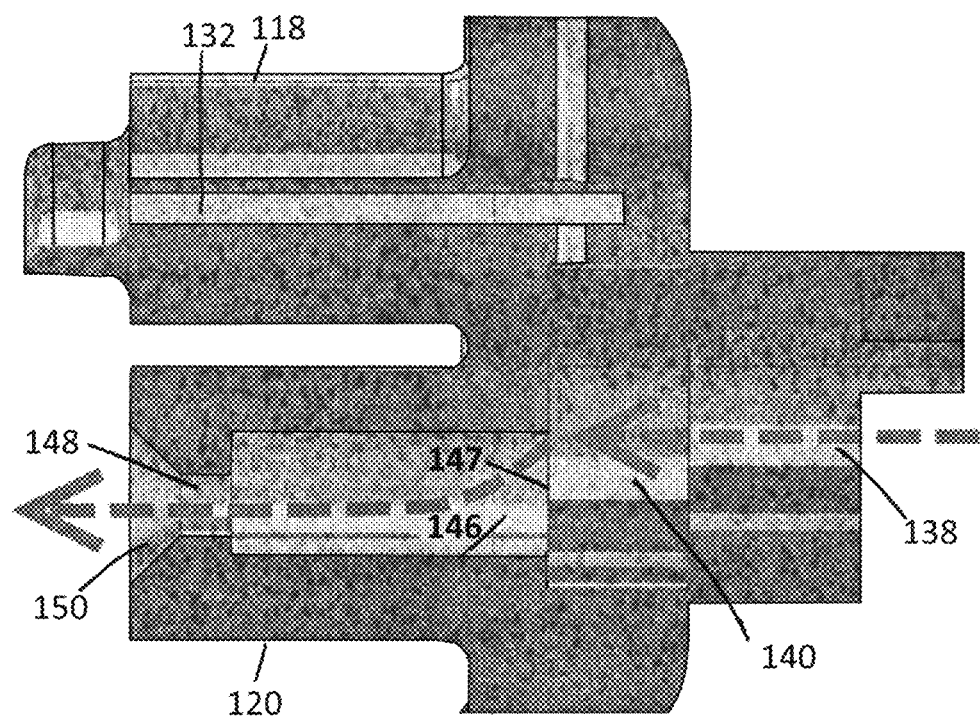
FIG. 13 is a cross-sectional view as in FIG. 11, showing internal gas flow in the single flow mode.

Valve housing 116 is configured whereby when valve body 134 is rotated into a first position, shown in FIG. 10 in which rear chamber is in its lowermost position, grooves 128 and 140 are aligned and form an internal passageway within diffuser 110 which is in fluid communication with rear chamber 140. Furthermore, rear chamber 140 is in fluid communication with inlet 147 of lower nozzle 120 in the first position. When valve body 134 is in this position, gas entering rear chamber 140 from front chamber 138 flows into both upper and lower nozzles 118 and 120, as seen in FIG. 11. Valve body 134 can also be rotated into a second position, as seen in FIGS. 12 and 13. In this position, rear chamber 140 is rotated away from its lowermost position and grooves 128 and 142 are out of alignment whereby they are no longer in fluid communication. In this rotational position, lower nozzle 120 remains in fluid communication with rear chamber 140 and gas continues to flow to the lower nozzle but gas flow is interrupted to upper nozzle 118. It will be seen that positions intermediate between these will allow the user to balance flow between upper and lower nozzles 118 and 120. Furthermore, continued rotation past the second position will attenuate the flow to lower nozzle 120 thereby allowing fine control over gas flow rates.

Figure 14:
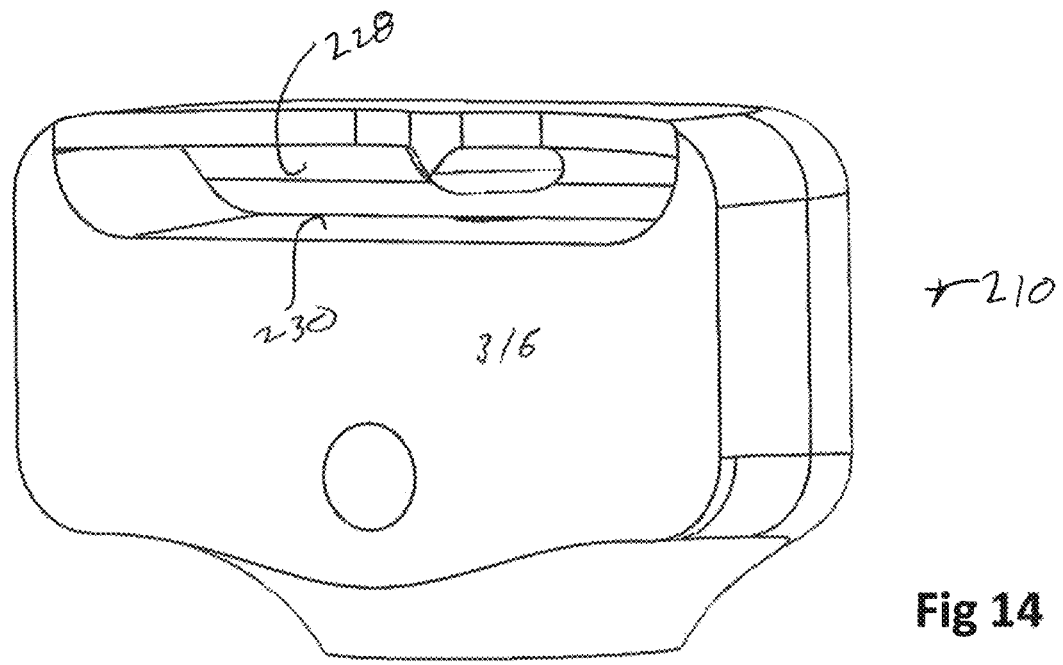
FIG. 14 is a perspective view of a diffuser according to a second embodiment.
Figure 15:
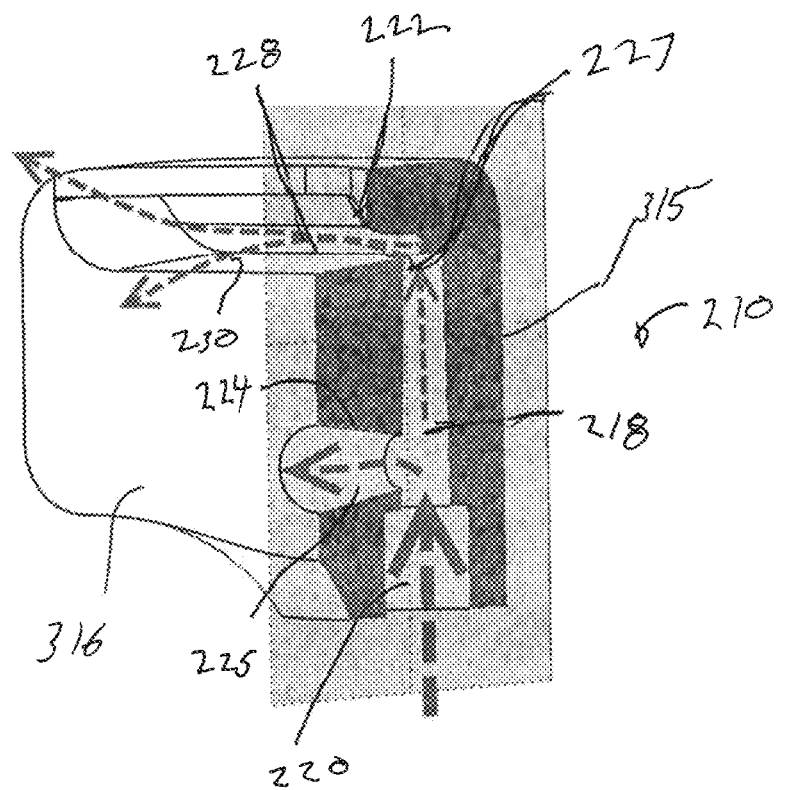
FIG. 15 is a view as in FIG. 14, partly in section, showing gas flow path through the diffuser shown in FIG. 14.
Figure 16:
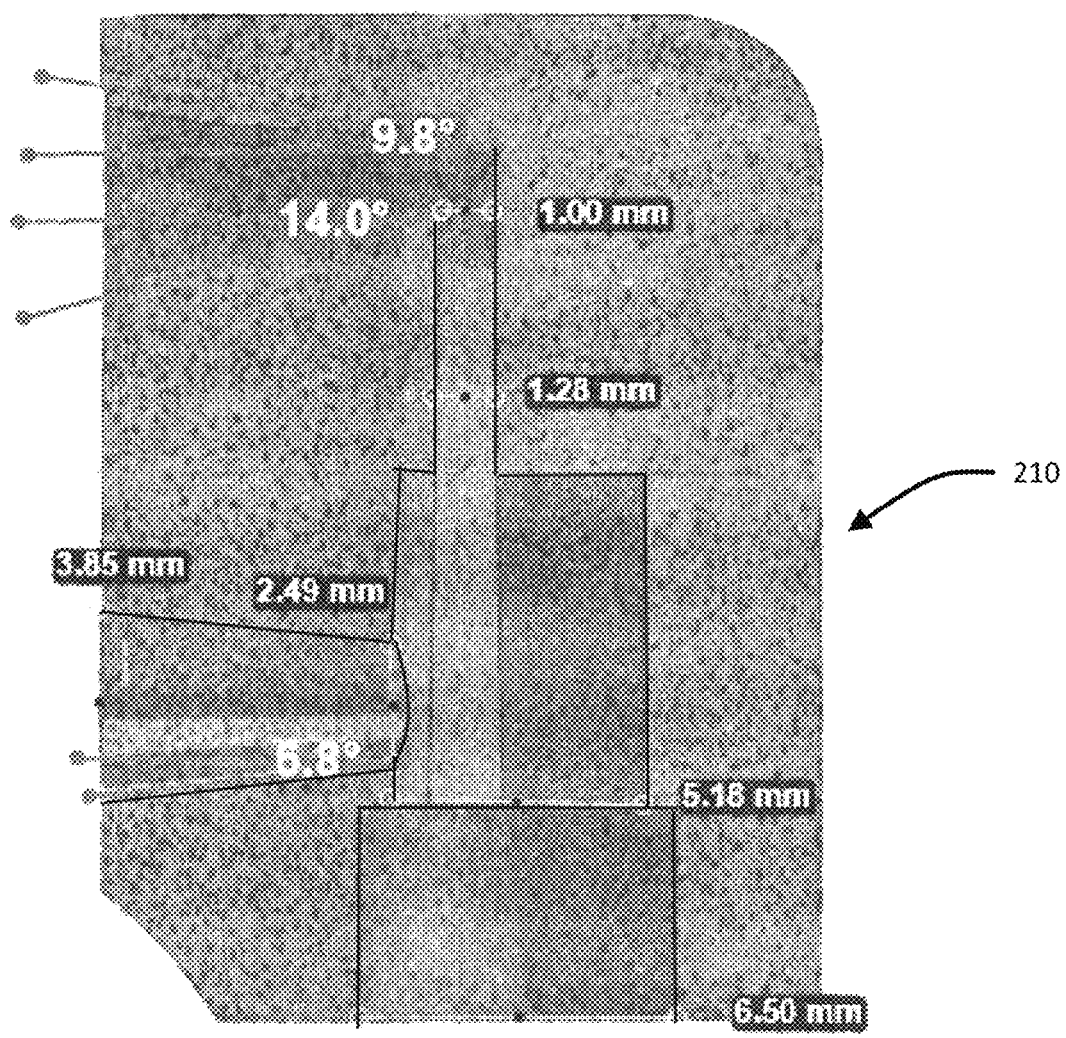
FIG. 16 is a cross-sectional view of the diffuser of FIG. 14, showing certain internal dimensions thereof.

FIGS. 14 to 16 show a further embodiment of a diffuser. According to this embodiment, diffuser 210 comprises a generally rectangular diffuser body for fitting within a diffuser retainer within the mask body (not shown) having a similar shape. However, as with the preceding embodiment, the configuration of the respective diffuser and retainer wall may comprise any convenient configuration and is not limited to the specific configurations of this example.

Diffuser 210 comprises generally parallel front and rear walls 315 and 316. A primary gas bore 218 extends vertically within diffuser 210 and terminates at its lower end in a gas inlet 220. Gas inlet 220 is configured to connect with an external gas source, not shown. Primary gas bore 218 is tapered whereby its inside diameter progressively narrows upwardly in the direction of gas flow.

Figure 20:
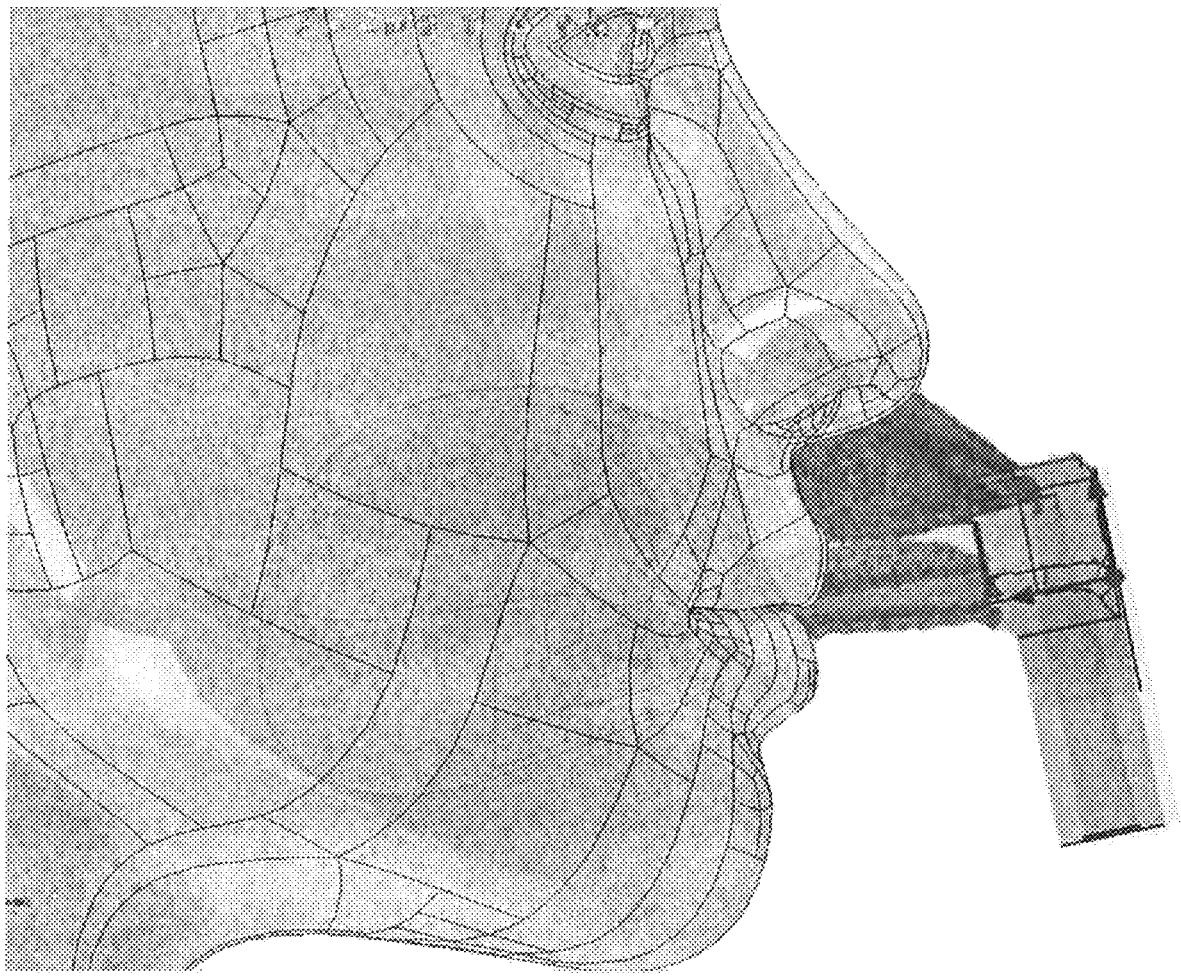
FIG. 20 is a flow simulation, showing simulated gas delivery concentrations when the present device is in use with a patient, with the mask body omitted for clarity.
Figure 20A:
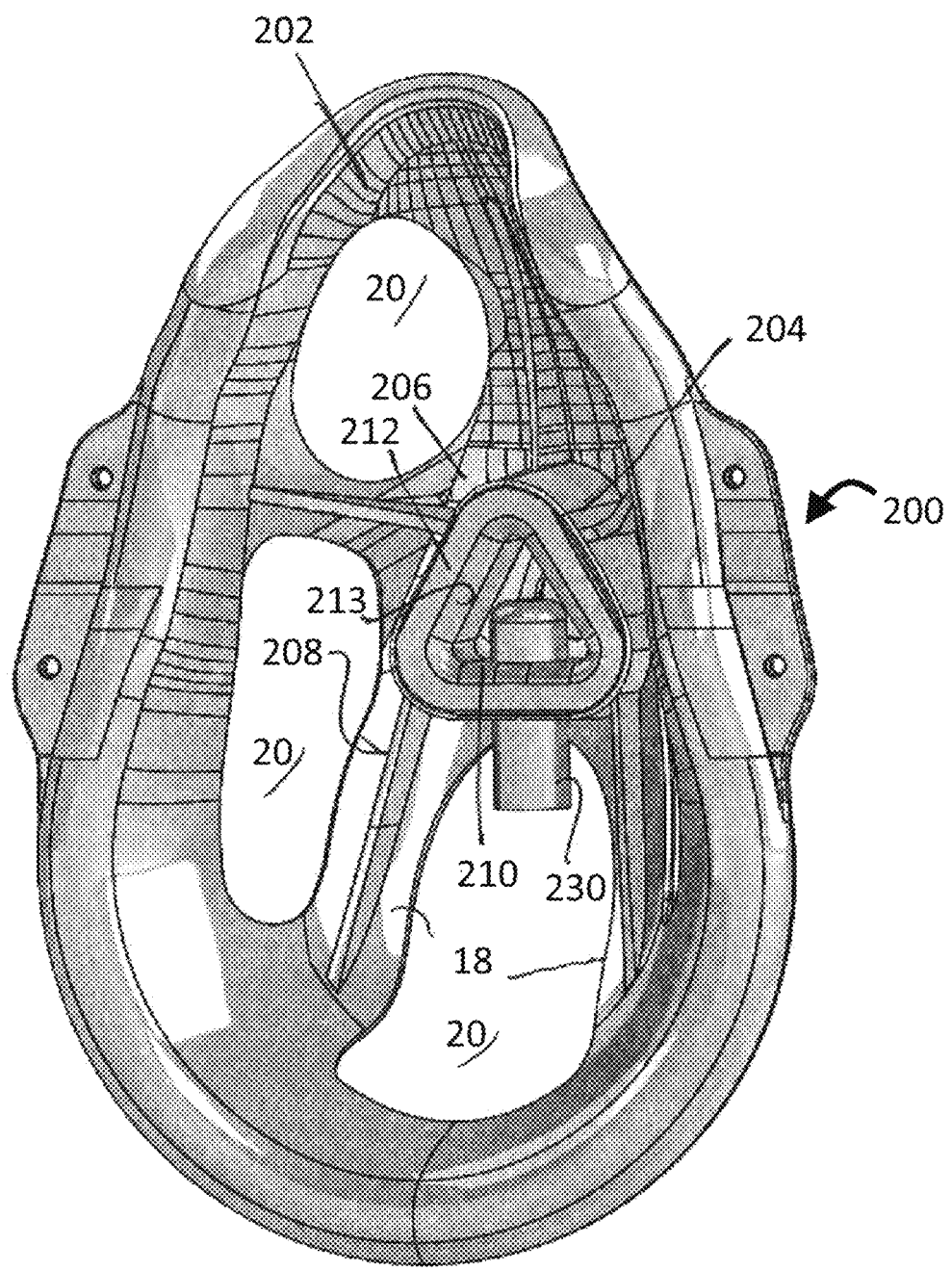
FIG. 20A is a perspective view, from the rear, of a further embodiment.

Diffuser 210 comprises upper and lower gas nozzles 222 and 224. Lower gas nozzle 224 comprises horizontal bore 225, which communicates internally with primary gas bore 218. Bore 225 tapers outwardly and rearwardly to generate a lower gas plume 100 towards the user's mouth (as seen in FIG. 20). As with the preceding embodiment, lower gas plume 100 is radially symmetric about its major axis and is relatively narrowly focused in comparison with the upper gas plume 102, described below.

Upper gas nozzle 222 is located adjacent to the top of diffuser 210 and comprises an elongate horizontal slot which opens rearwardly towards the user's face. Nozzle 222 has an internal opening 227 at its base which communicates internally with primary gas bore 218 and is configured to generate a gas plume directed towards the user's nostrils. Upper nozzle 222 is defined by upper and lower horizontal slot walls 228 and 230, in which the upper wall 228 is recessed (i.e. cut away) relative to the lower slot wall 230. In one configuration, upper slot wall 228 is arcuate. The recessed/cutaway portion serves to direct the upper plume 102 (see FIG. 12) upwardly towards the users nostrils, in a similar manner as the preceding embodiment. Furthermore, the upper and lower slot walls 228 and 230 are asymmetric about a vertical plane. Lower slot wall 230 is generally flat and slopes slightly downwardly and rearwardly. Upper slot wall 228 is curved upwardly and rearwardly. As such, the respective walls 228 and 230 of slot 226 diverge rearwardly towards the slot mouth.

FIG. 15 shows gas flow through diffuser 210, whereby incoming gas from the source enters diffuser through inlet 220 and into primary gas bore 218. A portion of the gas flows into lower nozzle 224 to form lower gas plume 100. The remaining gas flows into upper nozzle 222 to form upper plume 102.

FIG. 16 shows dimensions of an example of diffuser 210. According to this example, the inlet of primary gas bore 218 has an inside diameter of 6.5 mm and tapers to 1.0 at its upper end; and lower gas bore 225 has an inlet opening of 2.49 mm in diameter, tapering outwardly to an outlet opening of 3.85 mm in diameter. Lower gas bore has an outward taper of 6.8° from its horizontal axis. Upper slot wall 228 slopes upwardly at 9.8° from the horizontal and lower slot wall slopes downwardly at 14.0° from the horizontal. According to this example, these values can vary within a range of plus or minus 5%. According other examples, these values can vary within ranges of plus or minus 10%, 20%, 30%, 40% or 50%.

Figure 17:
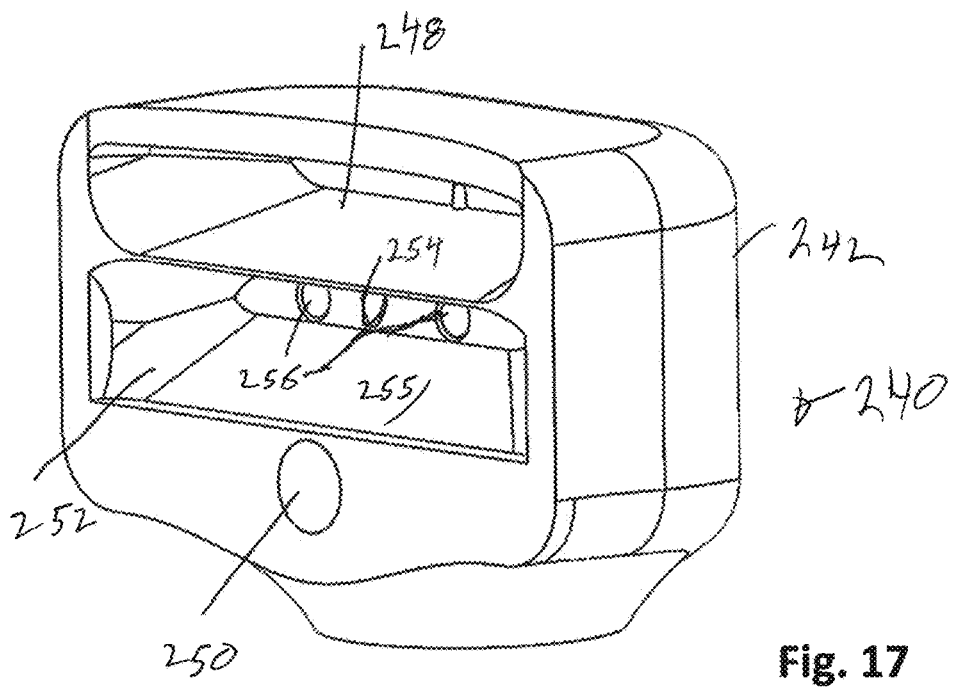
FIG. 17 is a perspective view of a further embodiment of a diffuser.
Figure 18:
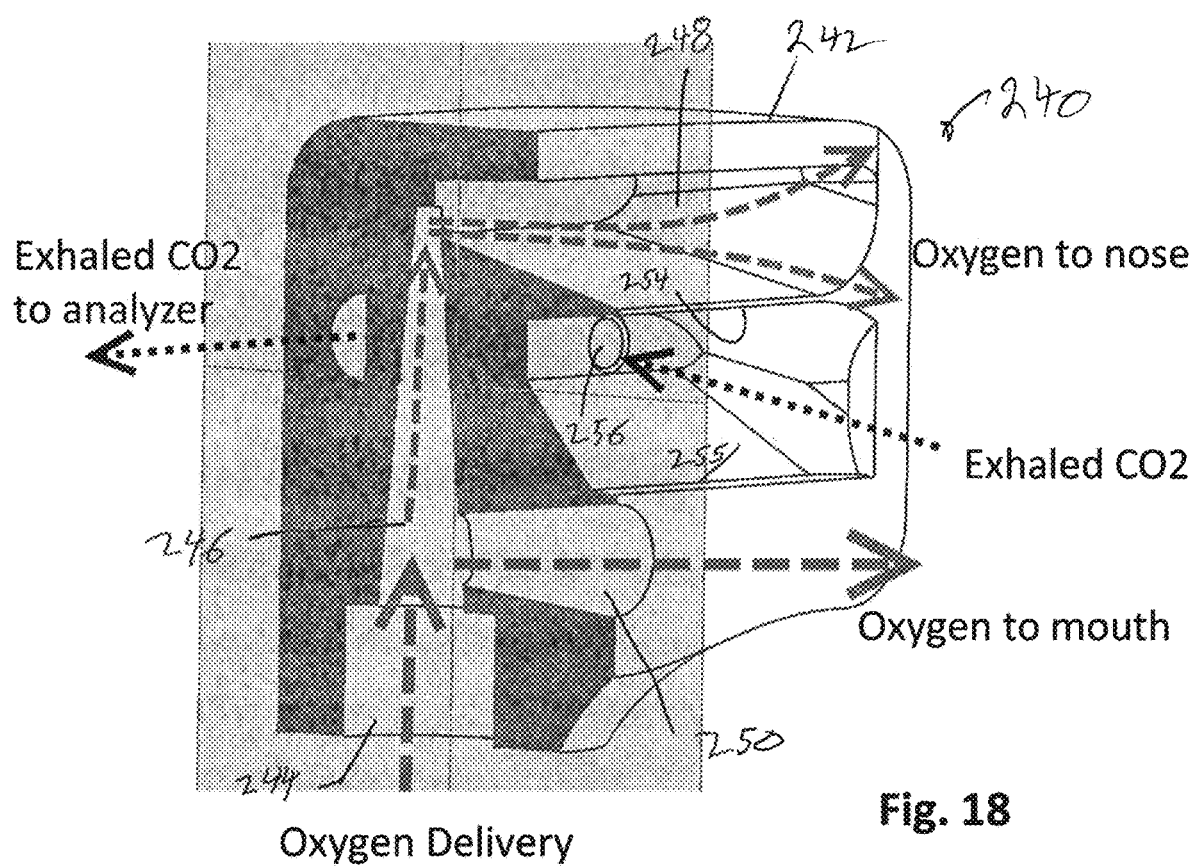
FIG. 18 is a perspective view, partly in section, of the diffuser of FIG. 17, showing gas flow path.
Figure 17A:
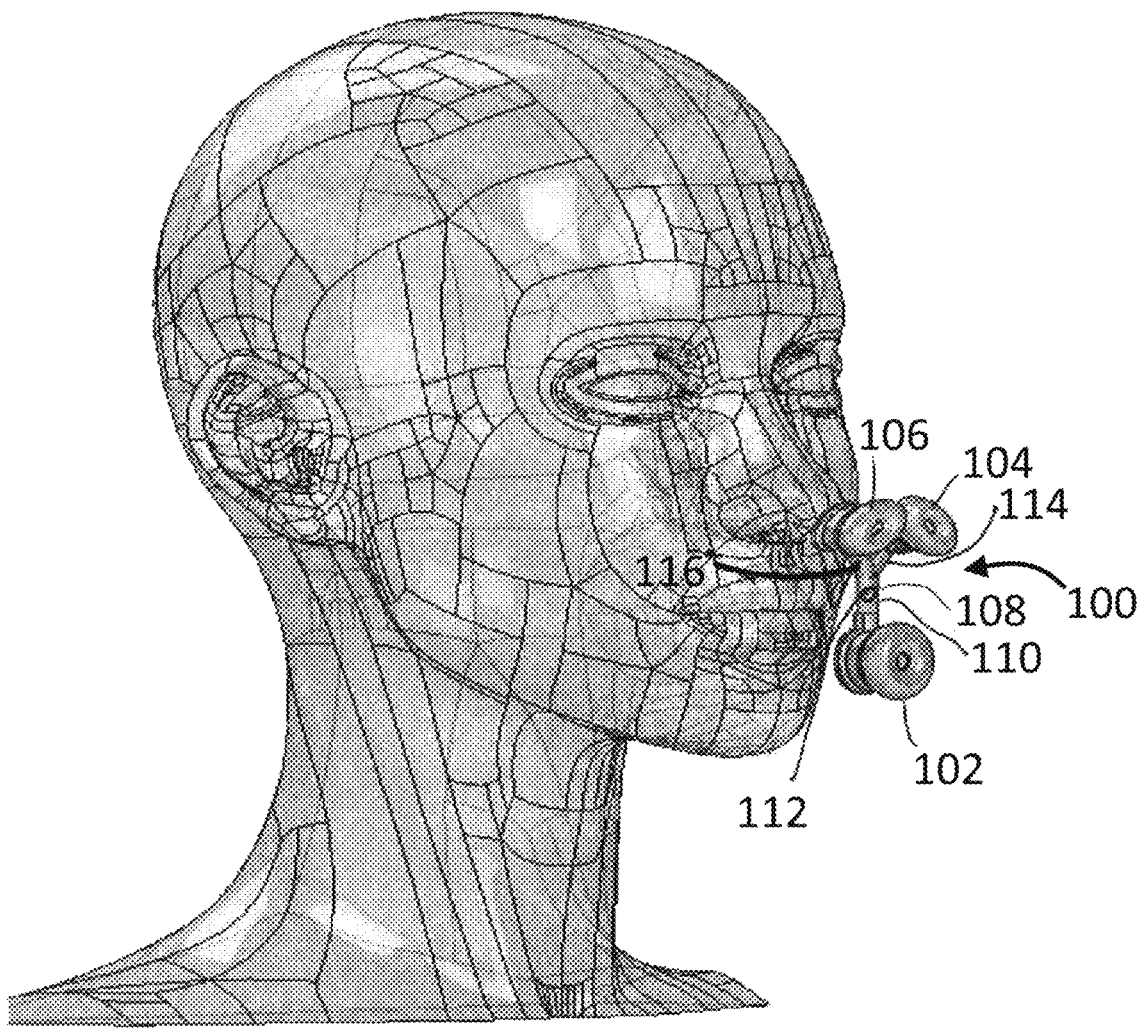
FIG. 17A is a perspective view of a further embodiment of the diffuser portion of the mask, showing its position relative to a patient. The mask body has been omitted for clarity.
Figure 18A:
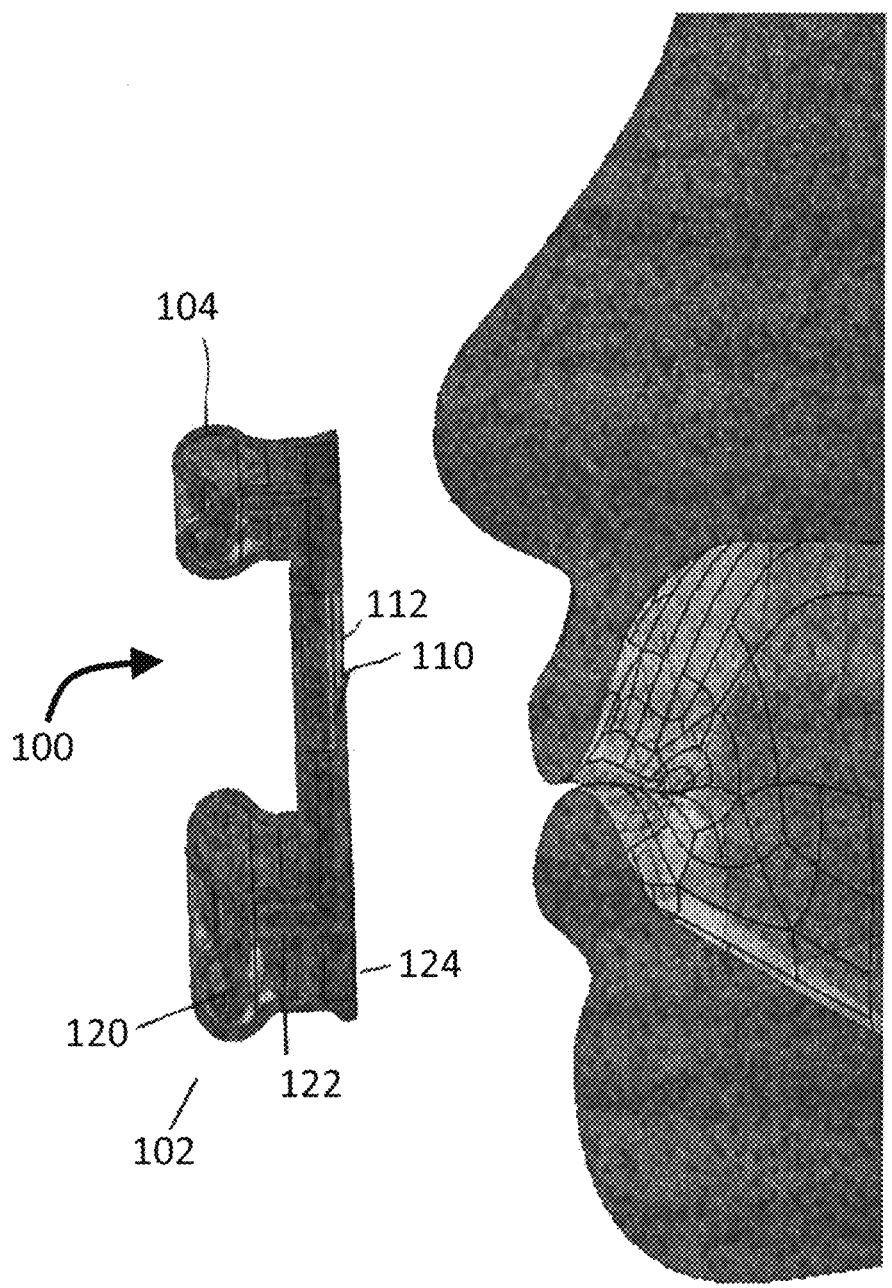
FIG. 18A is a sectional view from the side of the example of FIG. 17A.
Figure 19:
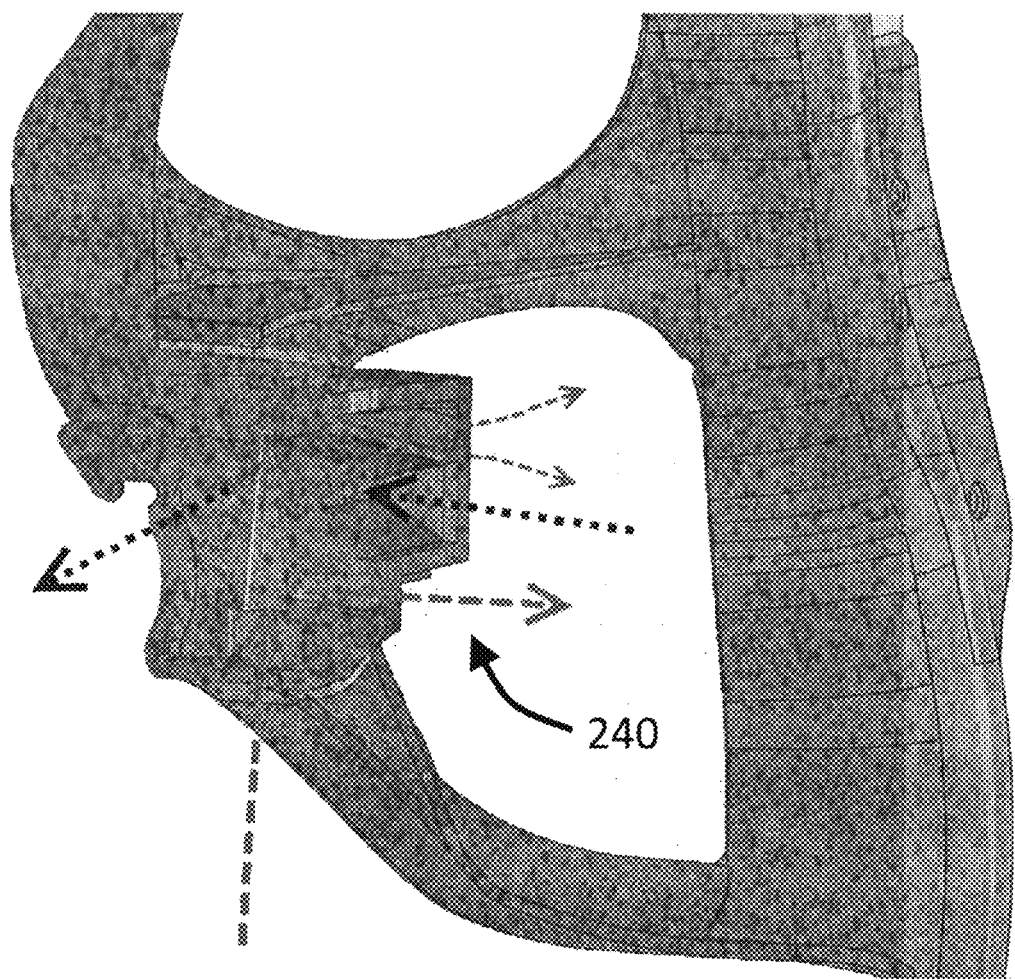
FIG. 19 is a perspective view, partially cut-away, of a mask and diffuser of FIGS. 17 and 18 showing gas flow through internal passageways.
Figure 19A:
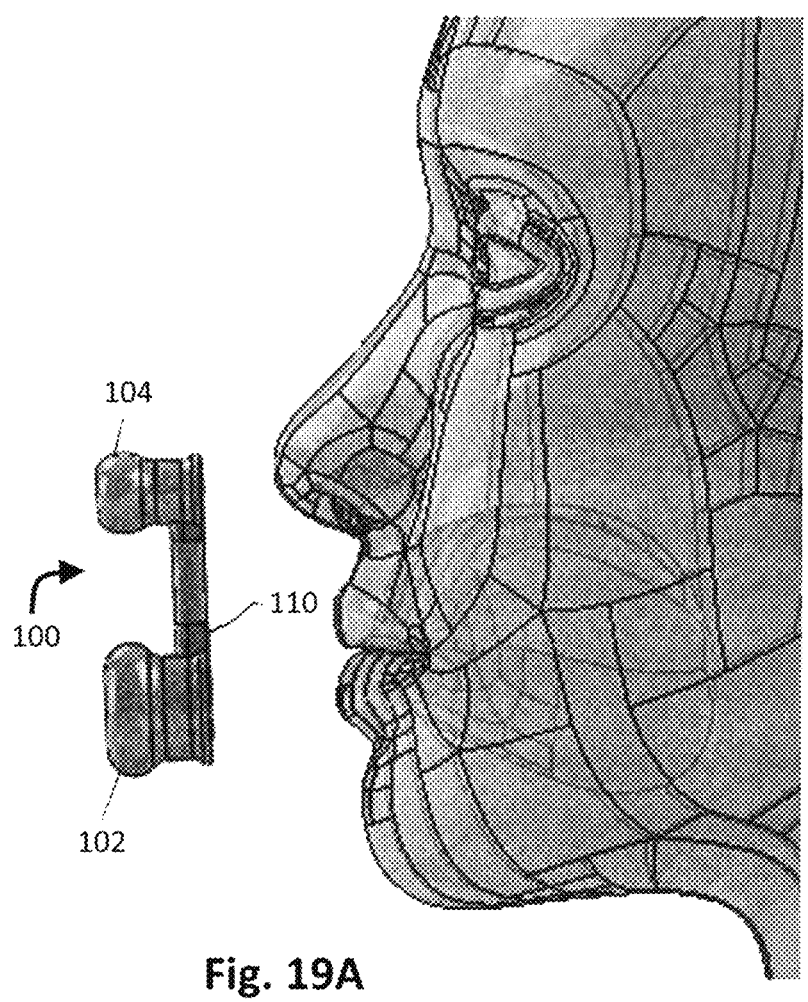
FIG. 19A is a side elevational view thereof.

A further embodiment of a diffuser 240 is shown in FIGS. 17 to 19. This embodiment is similar in overall configuration to the preceding embodiment of diffuser 210. Diffuser 240 comprises a diffuser body 242, a gas inlet port 244, an internal vertical bore 246 in fluid communication with port 244 and upper and lower outlet nozzles 248 and 250 in fluid communication with bore 246 and having the same configurations as the upper and lower nozzles 222 and 224 of the preceding embodiment.

Diffuser 240 further comprises an exhaled breath inlet port 252, to receive a portion of the exhaled breath of the patient (which normally has an elevated $CO_2$ content). Breath inlet port 252 comprises a horizontal slot opening towards the patient, and defined by upper and lower slot walls 254 and 255 that diverge outwardly and rearwardly. Port 252 comprises one or more outlet openings 256 at its base of slot, which in turn connect to an external $CO_2$ analyzer, not shown.

The respective lower and upper gas plumes 100 and 102 generated by diffusers 40, 110, 210 and 240 of the embodiments described herein are shown in computer-generated simulation in FIG. 20. It will be seen that the lower nozzle is configured to generate a relatively tightly focused radially symmetric lower gas plume 100, with a relatively narrow spread, which is directed horizontally towards the user's mouth. The upper plume 102 has a broader and shallower spread compared to the lower gas plume 100, and also is directed upwardly relative to a horizontal axis to impact on the user's nostrils.

Mask 10 is configured to be worn so as to substantially cover the patient's nose and mouth, whereby diffuser 40/110/210/240 is positioned between the user's nose and mouth. As seen in FIG. 20, diffuser 40/110/210/240 is generally centered over the user's mouth and positioned approximately 10 mm from this portion. When centered in this fashion, the upper and lower turbulent gas plumes are generally centered over the user's nose and mouth.

A further embodiment is shown in FIGS. 21 to 24, according to which a mask 300 is provided, having a mask body 302 which is similar in configuration to mask body 12 described above. A central diffuser retainer structure 304 is provided within hub 306 of mask body 302 and is configured to slideably retain a diffuser 312; diffuser 312 may be similar in structure to any the diffusers described herein. Alternatively, diffuser 312 may comprise a diffuser known to the art which is configured to fit within a mask body as described herein.

Retainer 304 includes a pair of spaced apart lower shelves 314a and b which protrude rearwardly from hub 206 to support the base of diffuser 304. A slot 316 is defined in the space between shelves 314a and b. Each shelf 314 has a downwardly extending slot wall 318a and b respectively at its inside edge whereby opposing walls 318a and b define the sides of slot 316. A pair of gussets 317a and b may be provided between shelves 314a and b and mask body 302 to stiffen shelves 314. Retainer 304 further comprises a pair of spaced apart guide walls 319a and b that project upwardly from shelves 314, aligned with slot walls 318a and b.

Diffuser 312 has a fin 320 that extends downwardly from its lower surface and is configured to fit within slot 316. Slot 316 thereby forms a guide for diffuser 312, such that diffuser slides in a fore and aft linear path, guided by fin 320 within slot 318. Diffuser 312 further comprises vertical slots, not shown, whereby guide walls 318a and b are slideably engaged within these slots to further guide diffuser 312 in a horizontal path.

Diffuser 312 can be slideably displaced between the fully extended position of FIG. 15, where it is relatively close to the user's face, and the fully retracted position shown in FIG. 16, where it is maximally displaced from the user's face, or any position between these. Diffuser 312 and retainer 304 are dimensioned to provide sufficient friction fit between these components to retain diffuser 312 in any selected position during normal use, while still permitting a typical user to slide diffuser 312 within retainer 304 to adjust its position. The position of diffuser 312 is selected to enhance user comfort, optimize gas flow properties and to accommodate facial features such as the user's nose. Adjustment of retainer 304 may be performed by a medical professional and/or the patient.

Figure 25:
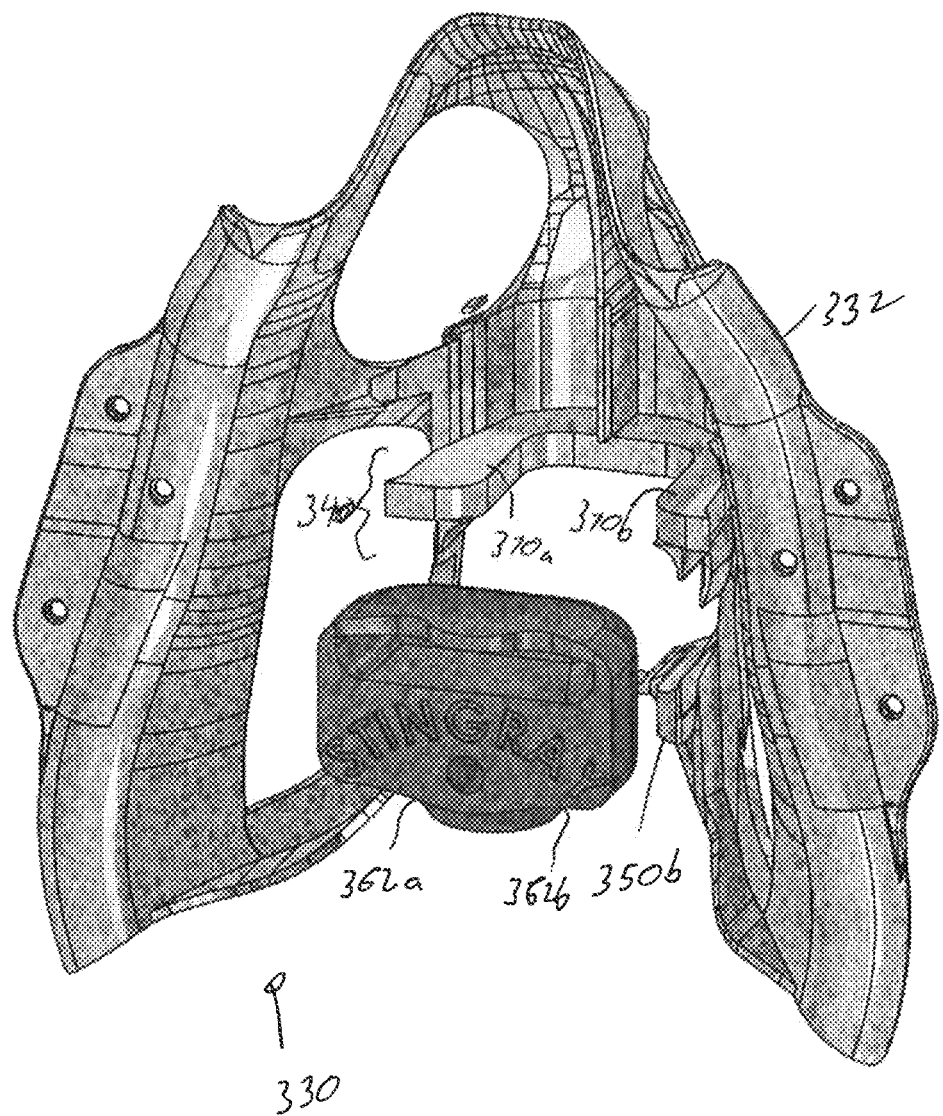
FIG. 25 is a perspective, exploded view of a further embodiment of the mask, showing an alternative structure for a sliding diffuser.
Figure 26:
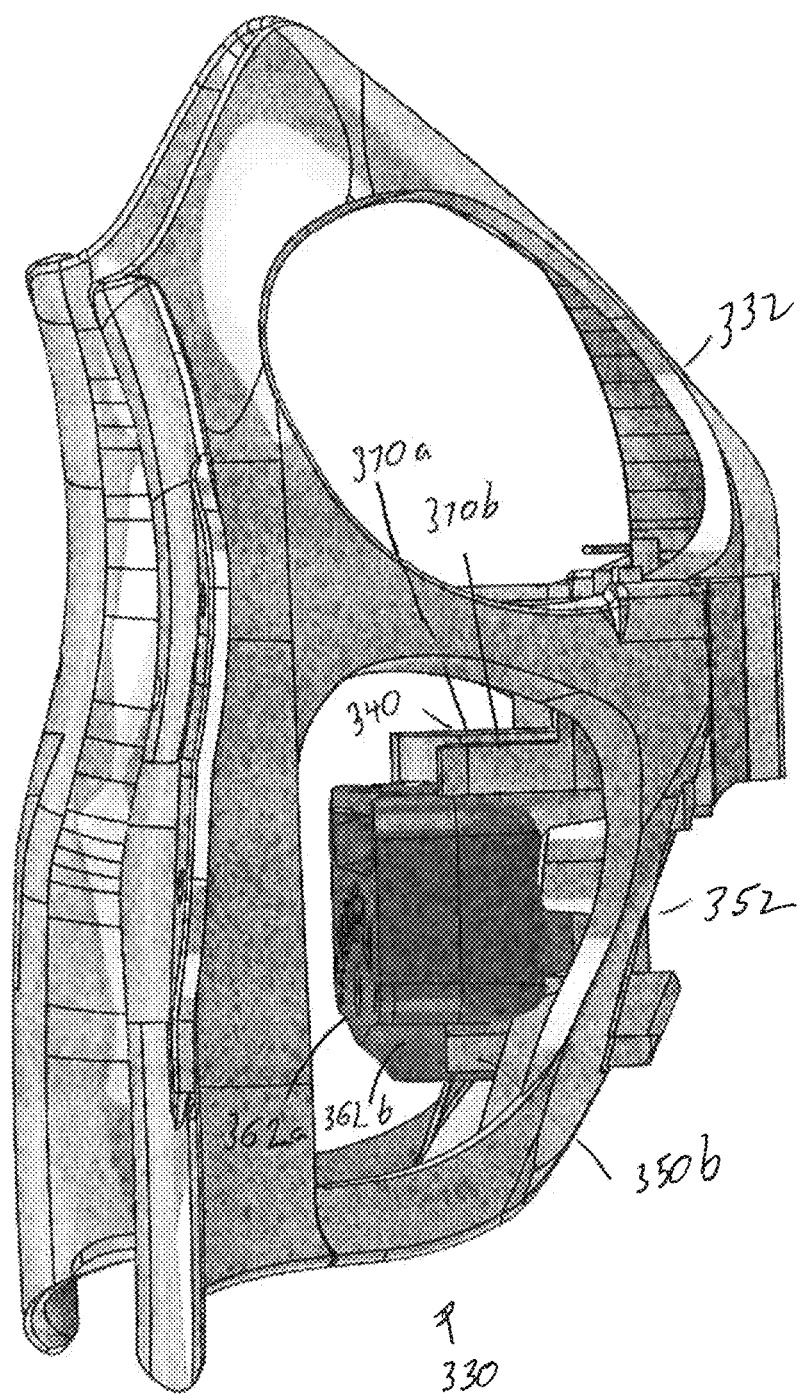
FIG. 26 is a side elevational view thereof, with the diffuser in the extended position.
Figure 27:
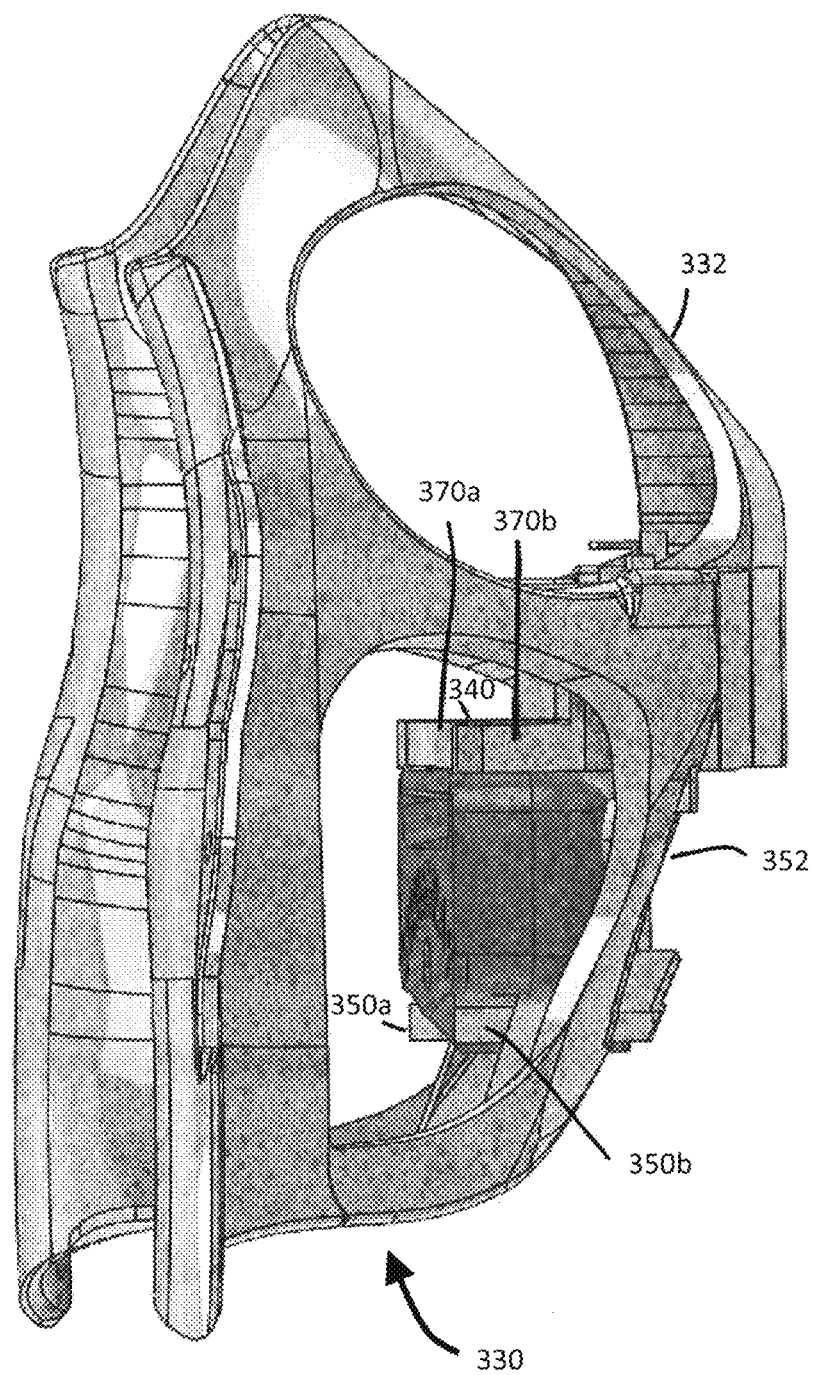
FIG. 27 is a side elevational view thereof, with the diffuser in the retracted position.

A further embodiment of a mask 330 with a linearly displaceable diffuser structure is shown in FIGS. 25 to 27. Mask 330 comprises a mask body 332 having a similar configuration to the mask bodies of the preceding embodiments. According to this embodiment, a central diffuser retainer 340 comprises spaced apart lower prongs 350a and b at its base, projecting rearwardly from hub 352 of mask body 332 and facing each other. Prongs 350 form ribs that engage corresponding recesses 362a and b within sidewalls 364a and b of diffuser 344. Retainer 340 further comprises spaced apart upper prongs 370a and b that parallel lower prongs 350a and b respectively. The respective upper and lower prongs 370 and 350 generally align with the respective corner edges of diffuser 340, whereby upper prongs 370 engage the upper surface of diffuser 344 and lower prongs 350 slideably engage grooves 362 of diffuser 344.

Diffuser 344 is slideably retained by friction fit within retainer 340 for displacement between retracted and extended positions, in a similar manner as the preceding embodiment. Diffuser 344 may be as disclosed herein, or it may comprise a diffuser known to the art which can be configured for independent attachment to the mask body.

Figure 28:
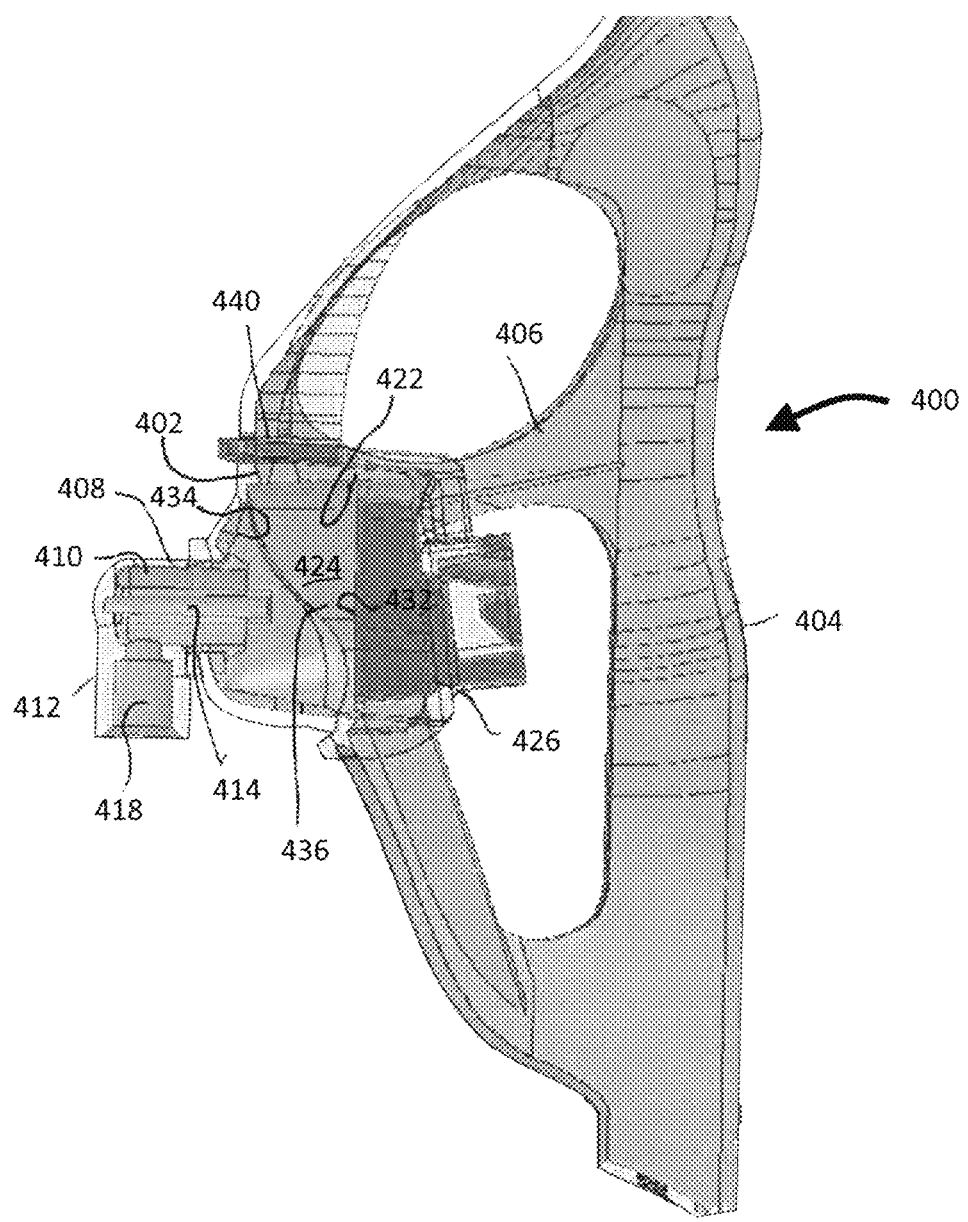
FIG. 28 is a cross sectional side view, in partial transparency, showing a further embodiment.
Figures 29, 30:
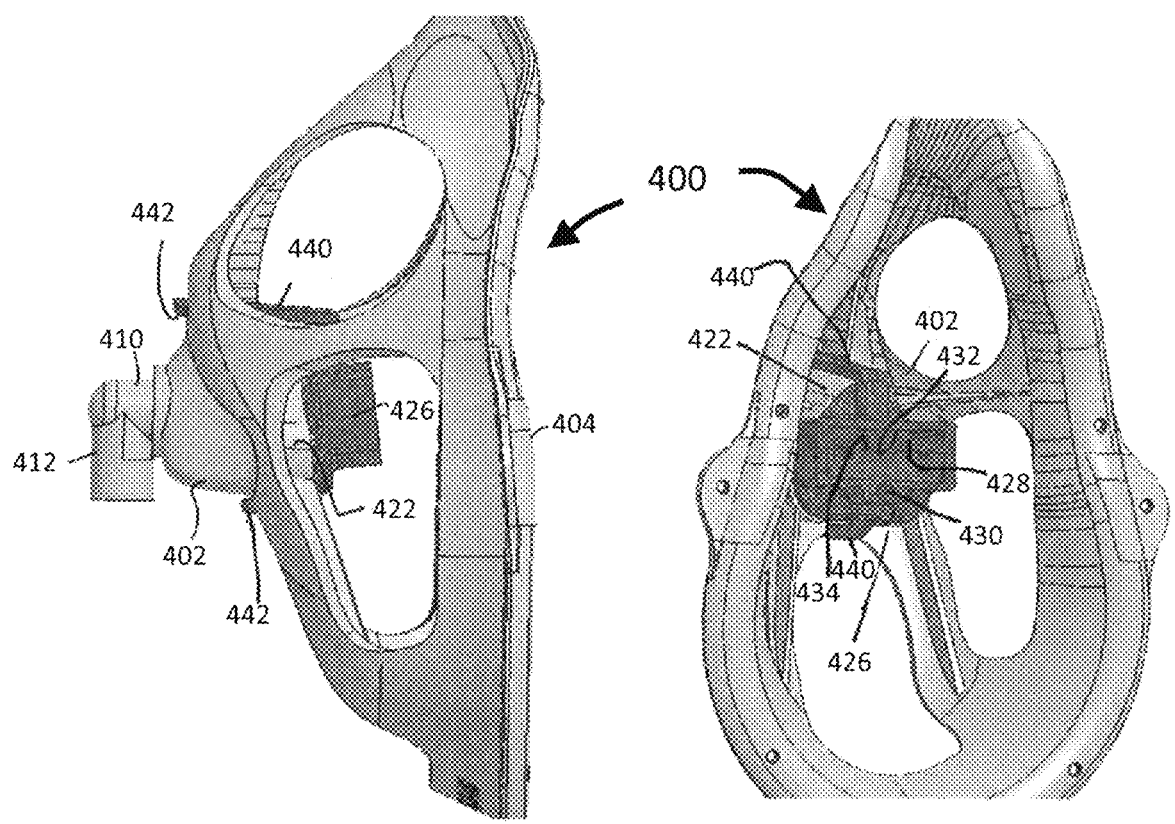
FIG. 29 is a side view thereof.
FIG. 30 is a perspective view thereof, from the rear.

FIGS. 28-30 show a further embodiment, comprising a mask body 400 having a central hub 402, a rim 404 and bridging portions 406 between hub 402 and rim 404. A gas inlet structure 408 protrudes forwardly from hub 402 and comprises a horizontal first leg 410 and downwardly-extending second leg 412. The first and second legs have internal bores 414 and 416 respectively that communicate internally. Second leg 412 terminates in a gas-tube connector 418 configured to connect to a gas supply tube, not shown. Mask body 400 comprises a wall 422 projecting inwardly from hub 402, which defines a receptacle 424. A diffuser 426 is retained within receptacle 424. Diffuser 426 is generally similar in structure to preceding diffuser 210 and comprises an upper, slot-shaped nozzle 428 and a lower conical nozzle 430. Upper nozzle 428 comprises upper and lower slot walls 432 and 434 that diverge towards the nozzle outlet. Lower nozzle 430 has a conical wall that likewise diverges towards its outlet. Upper and lower nozzles 428 and 430 open to the front face 432 of diffuser 426 to provide inlets to the respective nozzles. Nozzle 426 is secured within receptacle 424 whereby front face 432 of nozzle 426 is spaced from the floor 434 of receptacle 424 to provide a manifold 436 defined by the space between nozzle 426 and floor 434. Gas from internal bore 414 of gas inlet structure 408 discharges into manifold 436, and is in fluid communication with nozzles 426 and 428.

Diffuser 426 is retained to mask body 400 by a pair of resilient prongs 440, which extend forwardly from diffuser 426 at the upper and lower faces thereof. Prongs 440 are configured to extend around hub 402, and each terminate in a bulbous foot 442 that engages mask body 400. Diffuser 426 may be assembled with mask body 400 by inserting diffuser 426 into receptacle 424 whereby prongs 440 extend to the front side of hub 402 and feet 442 engage mask body 400. When engaged, the respective prongs 440 click into place to lock diffuser 426 to mask body 400 and prevent inadvertent release. Diffuser 426 may be removed by spreading apart prongs 440 to release diffuser 426 from mask body 400.

Referring to FIGS. 1A-3A, a mask 10 according to a first embodiment comprises a mask body 12, which comprises a flexible molded plastic wall having a concave interior. The exposed rim 14 of mask body 12 is pliable and is configured to contact the patient's face so as to substantially surround the nose and mouth region of a typical individual. Different mask sizes may be provided to accommodate, for example, adults, children, infants etc. The mask body may be similar in configuration to the mask body of the oxygen delivery masks described in U.S. Pat. No. 8,042,540 to McDonald et al. (incorporated herein by reference). According to this aspect, mask body 12 has a generally "open" structure composed of a centrally located hub 16 and portions 18a-c that radiate outwardly between hub 16 and rim 14. Areas 20a-c that are located between portions 18a-c and the areas of these combined may form about 30-80% of the surface area of mask body 12. Areas 20a-c comprise a central lower area 20a which is approximately opposed to a user's mouth and lateral open spaces areas 20b and c which are located on opposing sides of the user's nose bridge. Lower portions 18a and b define the lateral edges of lower area 20a and curve rearwardly towards the user's face at their lower ends. The exposed edges of mask body 12 that surround the area 20a define a curved plane.

Mask 10 may be secured to the patient by a strap or other such means, which are not shown but are generally conventional.

Mask hub 16 forms a forwardly projecting rounded snout region of mask body 12. The inside surface of this region defines an interior space 24 within mask body 12 which is opposed to the user's lower face. Hub 16 has a central opening 38 to accommodate a diffuser assembly 39, which projects through opening 38 to protrude both forwardly and rearwardly from mask body 12 at hub 16.

According to one aspect, mask body 12 is molded as a single monolithic structure that includes rim 14, hub 16, bridges 18, wall 32 and optional ribs 34. Alternatively, these components may comprise different materials, for example by assembly from individual components or by using a multi-density molding process. For example, the respective components may comprise different densities, resilience or other properties. In one aspect, bridges 18 comprise a material that is sufficiently rigid to dispense with the need for stiffening ribs 34.

Diffuser assembly 39 may comprise a structurally independent, rigid plastic member that is assembled to mask body 12, or alternatively it may be co-molded with mask body 12. Diffuser assembly 39 projects through opening 38 within hub 16 whereby a first portion 42 of assembly 39 is external to mask body 12, i.e. projecting forwardly from body 12, and a second portion 44 of diffuser assembly 39 projects rearwardly into the interior of mask body 12 towards the user's face. The respective internal and external portions 42 and 44 are aligned along a central horizontal axis "a" of diffuser 40 (see FIG. 5A). In the embodiments in which diffuser assembly 39 comprises a structurally independent component from mask body 12, it may be secured within opening 38 by adhesive, friction fit or other fastening means to mask body 12.

The interior portion 44 of diffuser assembly 39 includes a peripheral wall 32 that projects rearwardly towards the user's face. Wall 32 encircles a generally triangular region to define a receptacle 34, which opens towards the user's face. Wall 32 may have any configuration that is suitable for retaining a central diffuser 40, described below.

Figure 2A:
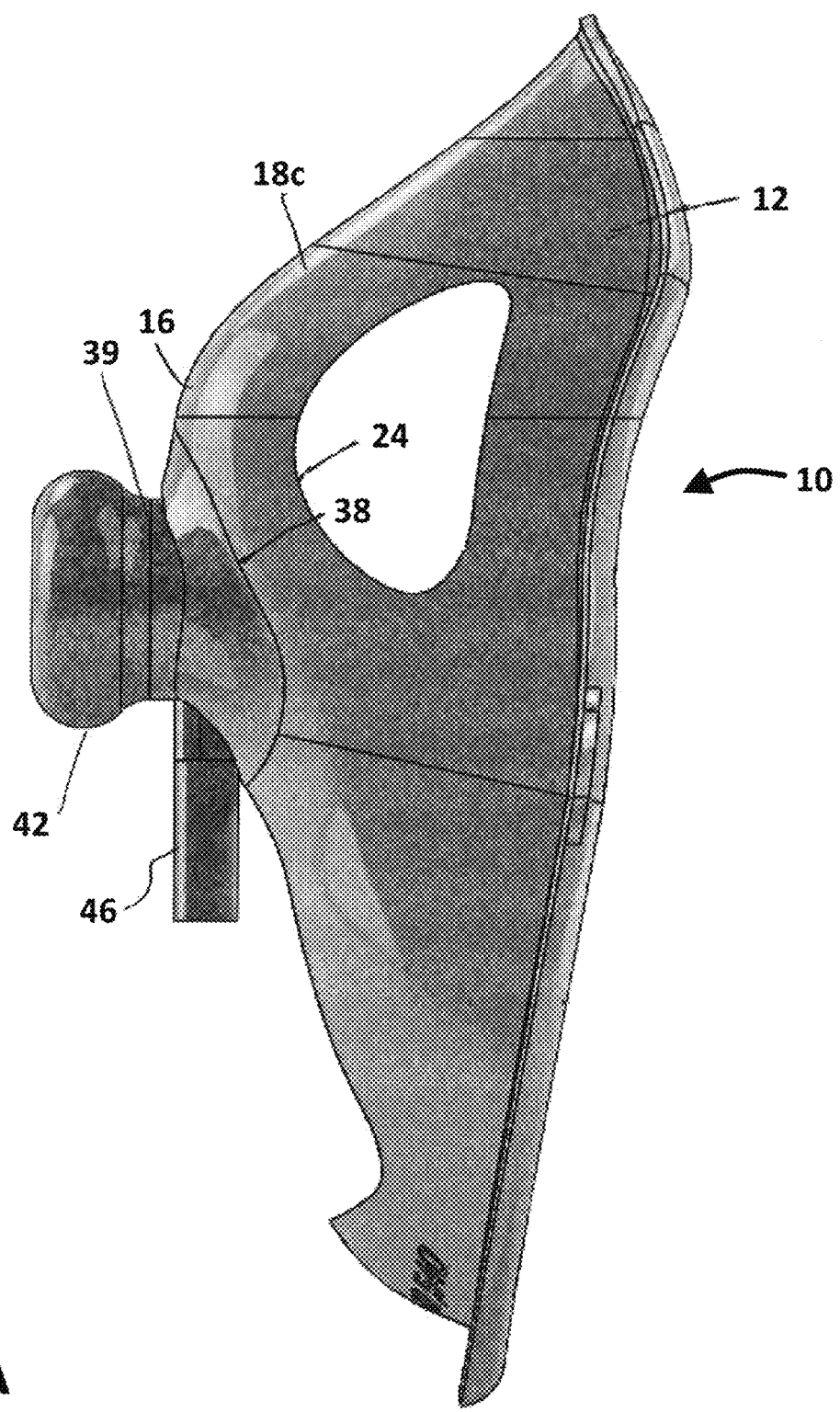
FIG. 2A is a side elevation view of the same.

As seen in FIGS. 4A, 5A, 10A and 11A, diffuser assembly 39 includes a central diffuser 40 for generating a plume of concentrated gas within mask body 12. Diffuser 40 is generally cylindrical in configuration and comprises a generally cylindrical sidewall 41 merging with a bulbous end wall 43 at the forward end. The respective walls 41 and 43 define a hollow interior space 45. Diffuser assembly 39 further comprises a downwardly-extending gas inlet conduit 46, having a vertically-oriented inlet bore 48, in fluid communication with the interior of diffuser 40. At its upper end, conduit 46 extends into the interior 45 of diffuser 40. At its lower end, conduit 46 extends to a position which is adjacent to lower opening 20a of mask body 12 (see FIGS. 2A and 3A) whereby an oxygen tube (not shown) can connect with conduit 46.

Diffuser 40 comprises an internal axial gas tube 50, having a bore 52 which is coaxial with axis "a". Bore 52 connects internally with vertical inlet bore 48 at an elbow 53, whereby a gas flow is directed from an external source (not shown) through inlet bore 48 and into axial gas tube 50, which are all in fluid communication. Axial tube 50 has a mouth 54 which opens into the interior space 45 of diffuser 40 to discharge gas forwardly, away from the user's face and towards an inside surface 65 of end wall 43 of diffuser 40. Gas entering diffuser 40 through inlet 46 conduit follows an initial upward path through vertical bore 48, followed by a horizontal forward path through axial bore 52, leading away from the users face.

The first portion 42 of diffuser 40 has a hollow interior defined by inside surface 65 with a generally torus-shaped configuration, which forms a gas rebound chamber 60. The inside surface 65 of end wall 43 includes a central cone 62 with a rounded shape (resembling a rounded dome), protruding rearwardly within chamber 60. Cone 62 is directly opposed to and spaced from mouth 54 of bore 52, so as to be co-axial with axis "a" and to function as a gas flow spreader. The term "flow spreader" refers to a structure which evenly spreads the flow of gas in a laminar flow pattern whereby the radius of the gas flow stream is increased. Gas flow is discharged from mouth 54 and impinges on cone 62. The resulting gas flow is then spread evenly outwardly along the surface of cone 62 to flow in a laminar flow path over cone 62. Cone 62 is surrounded by torus-shaped gas rebound chamber 60, which is defined by the rounded inside surface 65 of end wall 43. As discussed below, surface 65 performs a gas-rebound function which deflects the forwardly-flowing gas stream so as to reverse the direction of gas flow back towards the user's face in a rearward direction.

The configuration of diffuser 40 and in particular gas rebound chamber 60, according to one aspect, retains the gas flow in a laminar flow pattern as the gas impacts surface 65 and is rebounded rearwardly towards the patient.

Referring back to FIGS. 1A-5A, the second portion 44 of diffuser 40, projecting rearwardly from the first portion 42, comprises an essentially cylindrical wall which has a smaller radius than the first portion and defines a narrowed throat 66 which is co-axial with axis "a". Axial tube 50 extends longitudinally through throat 66, whereby throat 66 has an annular configuration.

Figure 4:
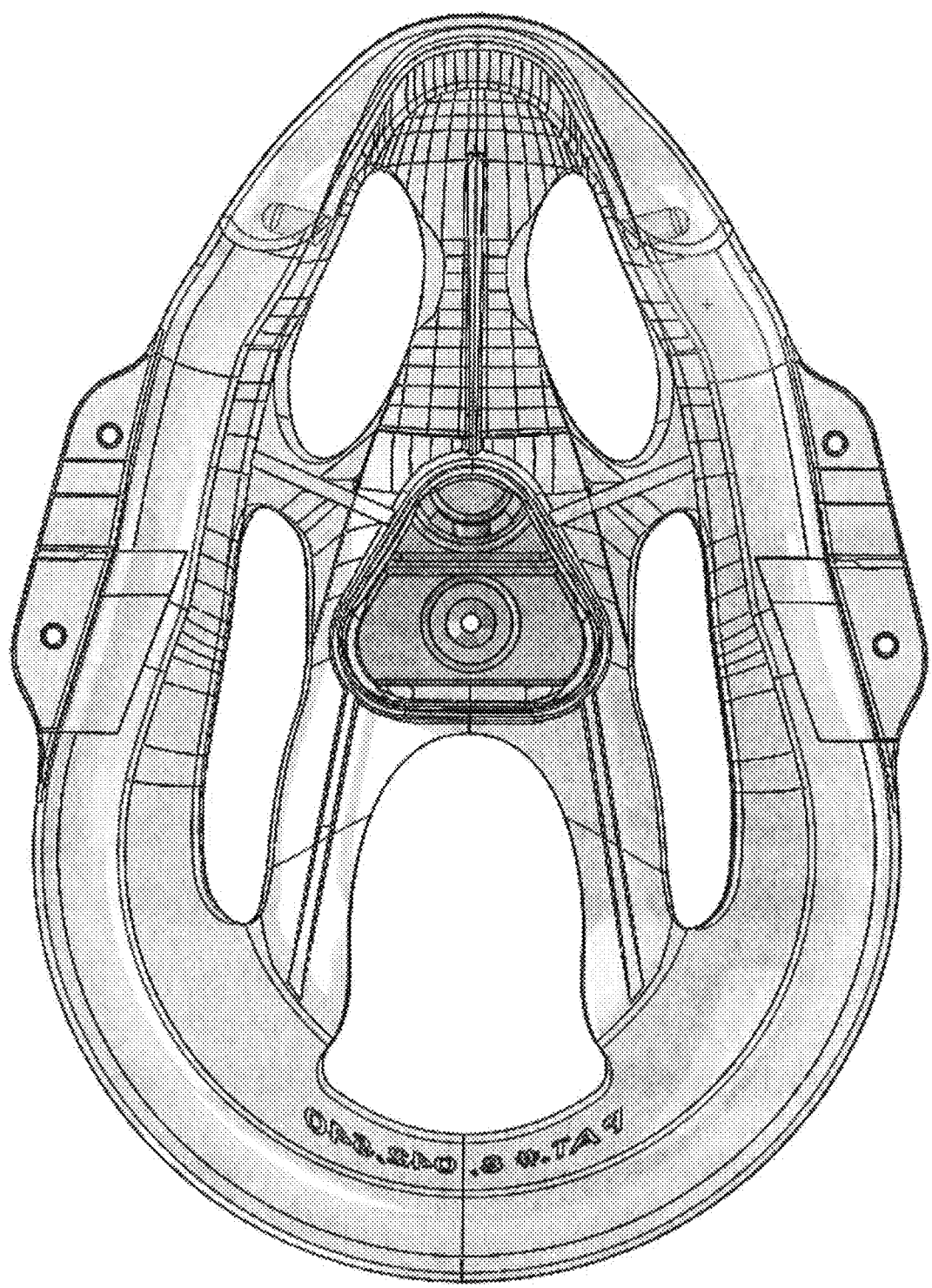
FIG. 4 is a rear view, showing the interior of the mask body and diffuser.
Figure 4A:
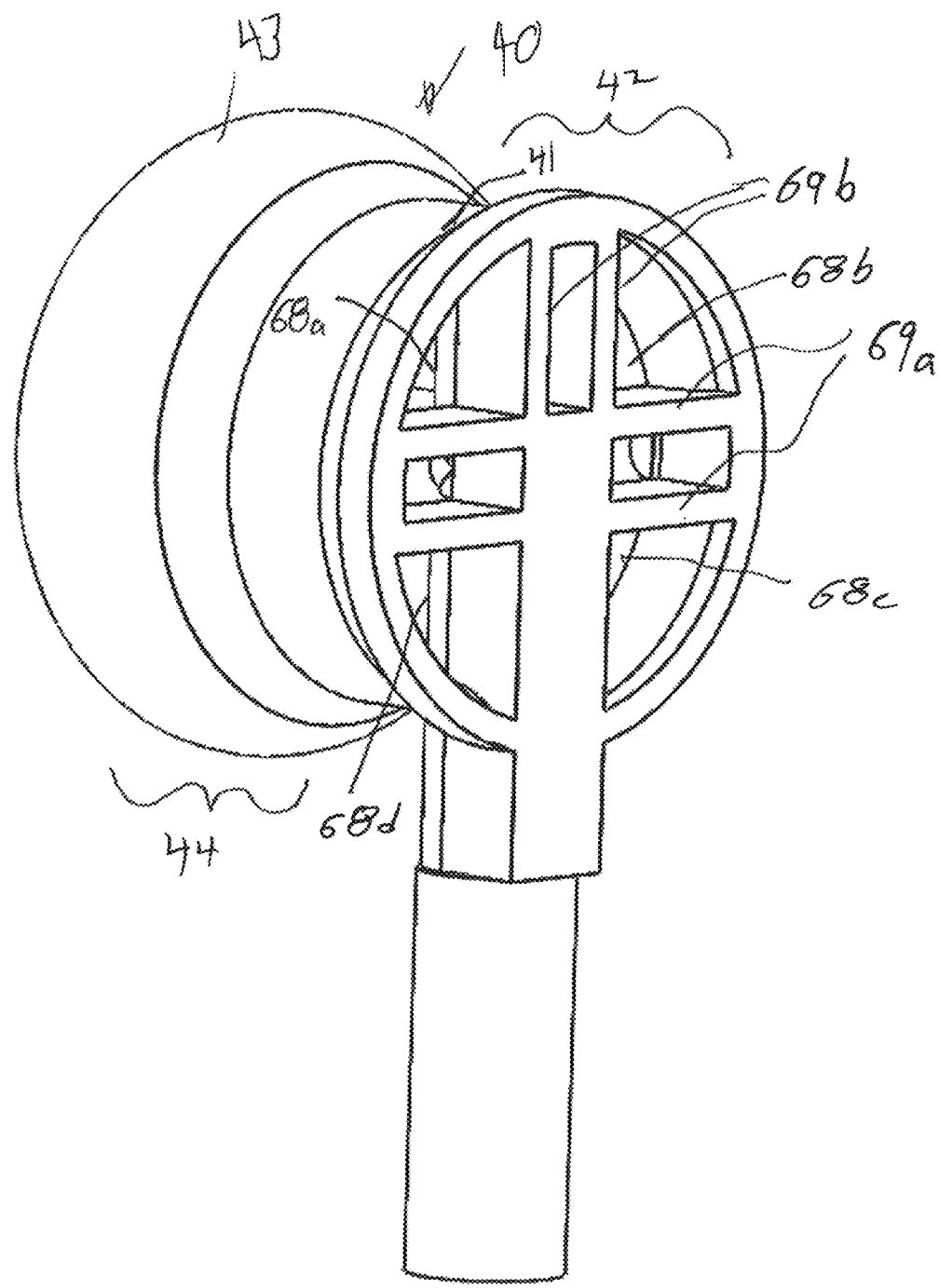
FIG. 4A is a perspective view of the diffuser component of the mask, seen from the rear.
Figure 6:
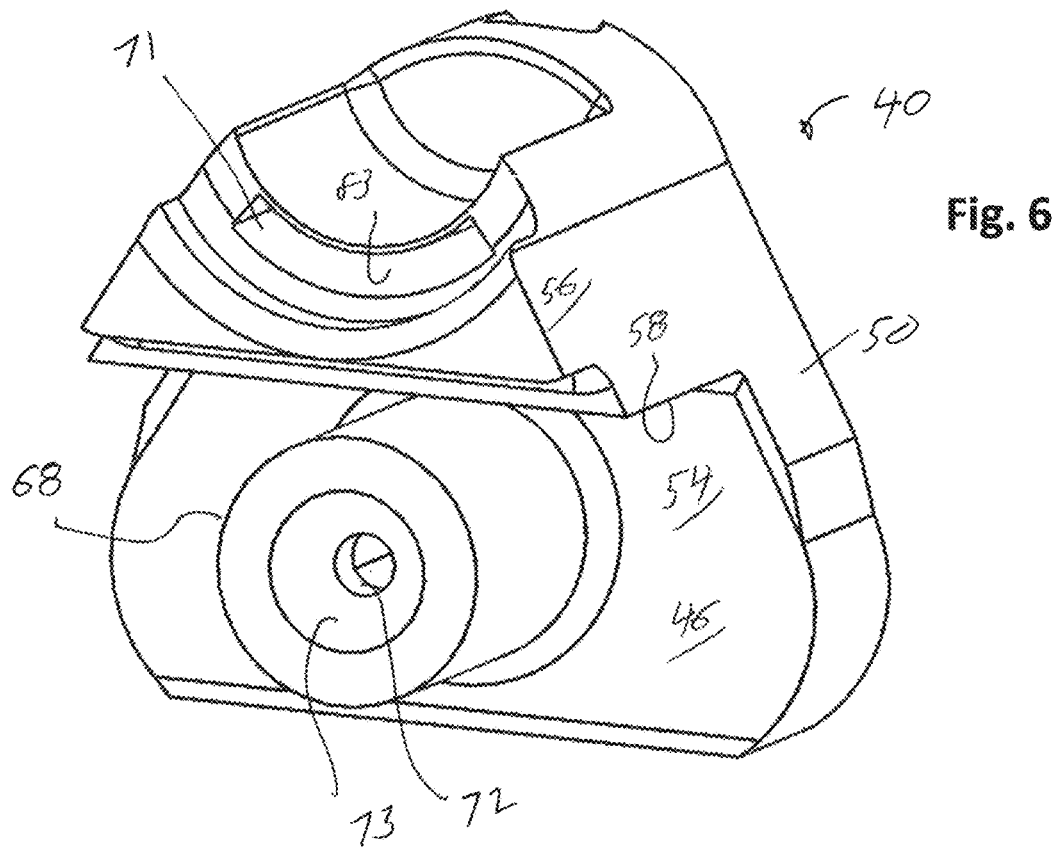
FIG. 6 is a further perspective view of the diffuser from the rear.

Throat 66 terminates at its rearward end in four gas outlet ports 68a-d, which are distributed radially around throat 66. Ports 68 are defined by horizontal and vertical paired septums 69a and b within throat 66, which divide throat 66 into the four ports 68. Furthermore, internal walls 71 between the septum pairs block portions of throat 66 to channel airflow into ports 68a-d. Ports 68a-d discharge gas flowing through throat 66 towards the user's face. As seen in FIG. 4A, two of outlet ports 68a and b are located above the midline of throat 66, for directing oxygen towards the user's nose, and two of ports 68c and d are located below the midline of throat 66 for directing oxygen towards the user's mouth. Optionally, outlet ports 68a and b are configured to redirect a portion of the oxygen flow upwardly towards the user's nostrils and/or lower ports 68c and d are configured to redirect a portion of the gas flow downwardly towards the user's mouth.

Figure 5:
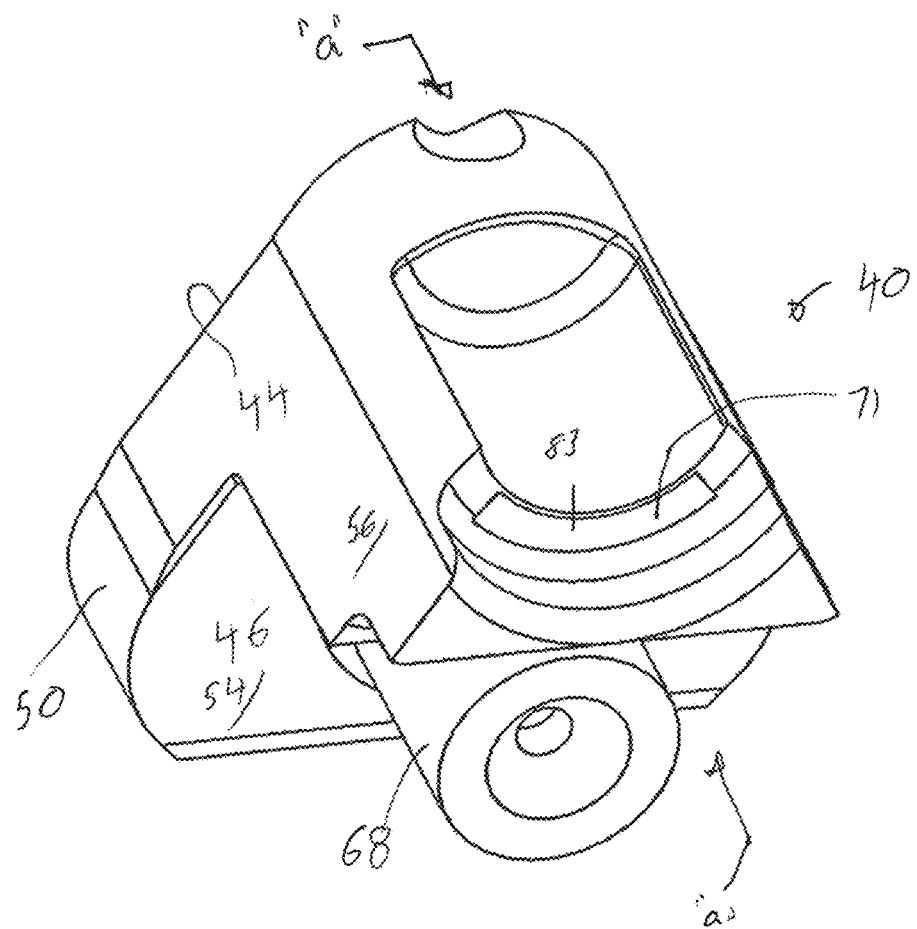
FIG. 5 is a perspective view, from the rear (i.e. from the perspective of a user of the mask), of the diffuser component of the mask.
Figure 5A:
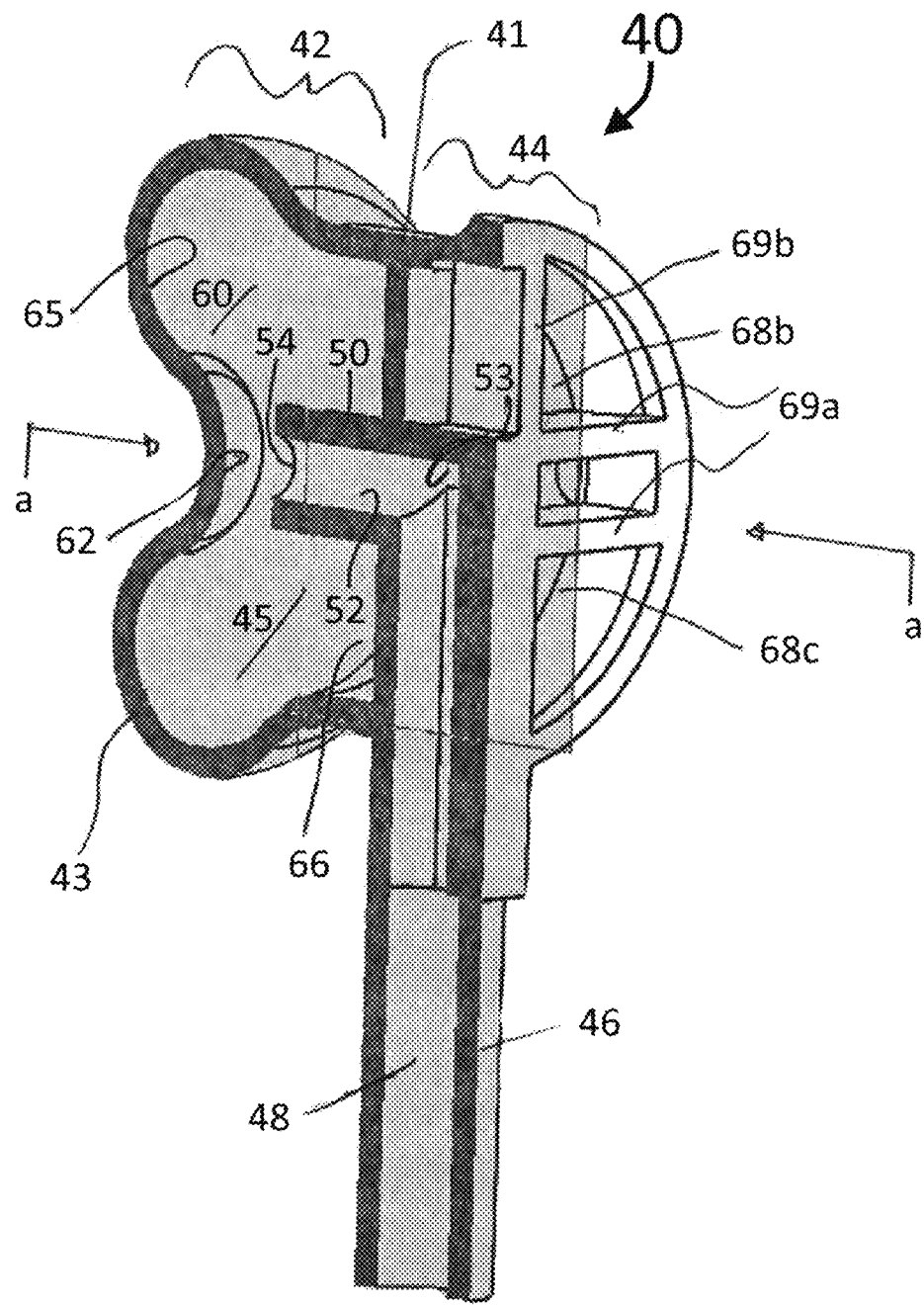
FIG. 5A is a cutaway view of the diffuser showing internal structure and the gas flow path.
Figure 6A:
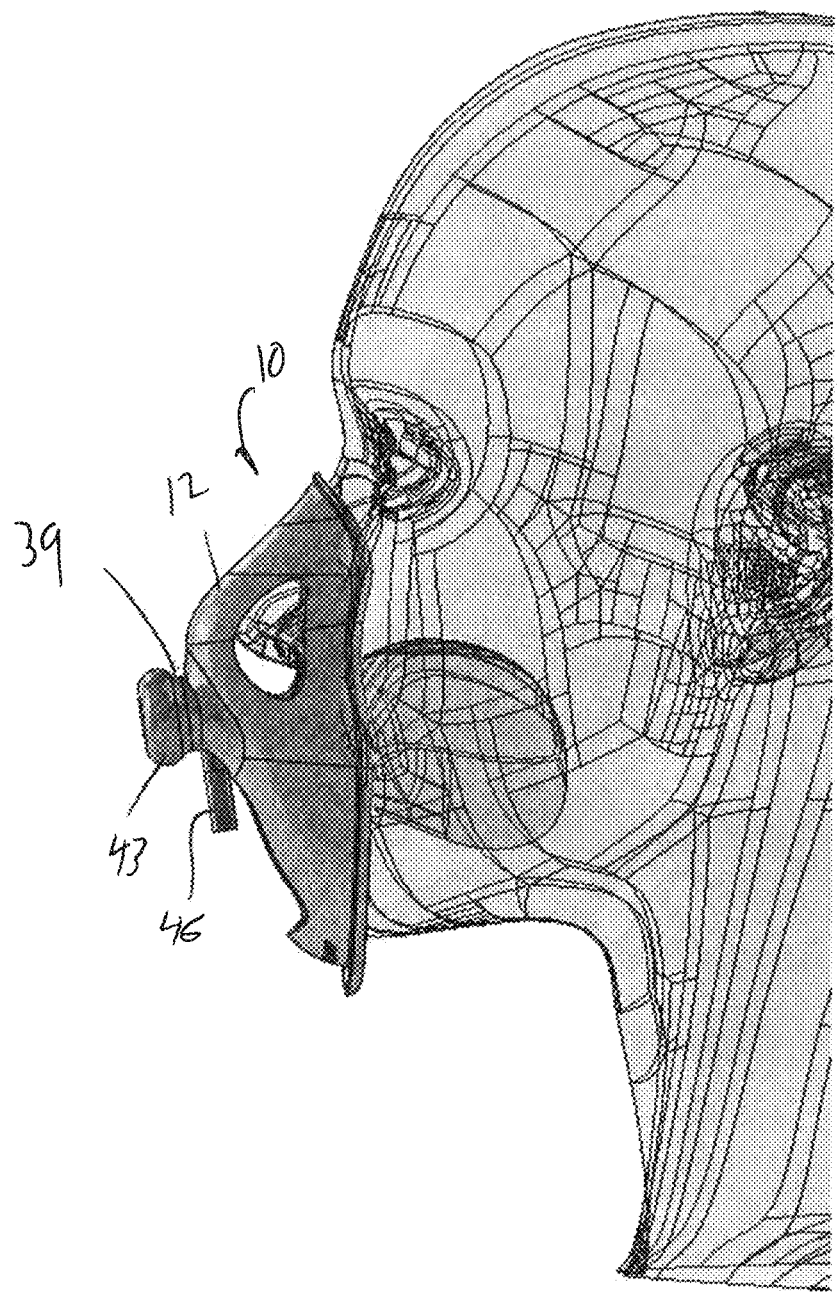
FIG. 6A is a side view, showing the mask in use on a patient.
Figure 7A:
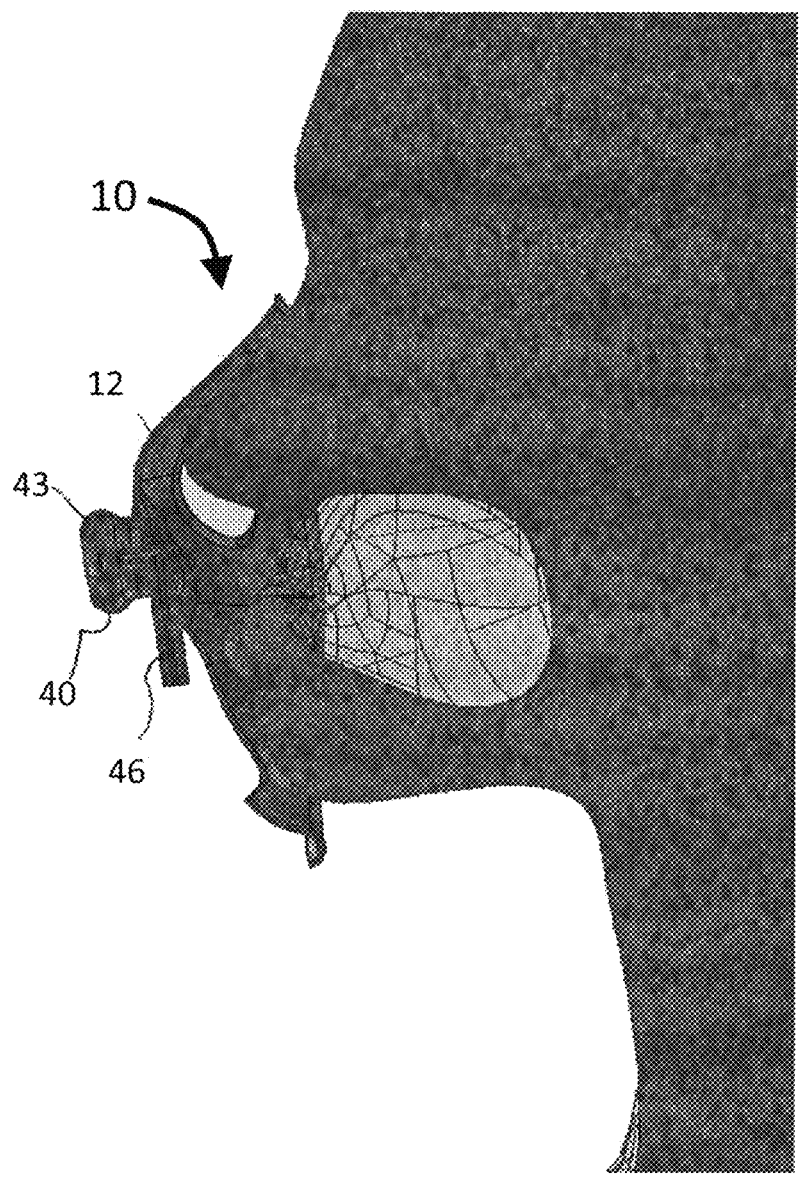
FIG. 7A is a further side view, in section, showing the mask in use on the patient, and showing internal structure of the mask and diffuser.
Figure 8A:
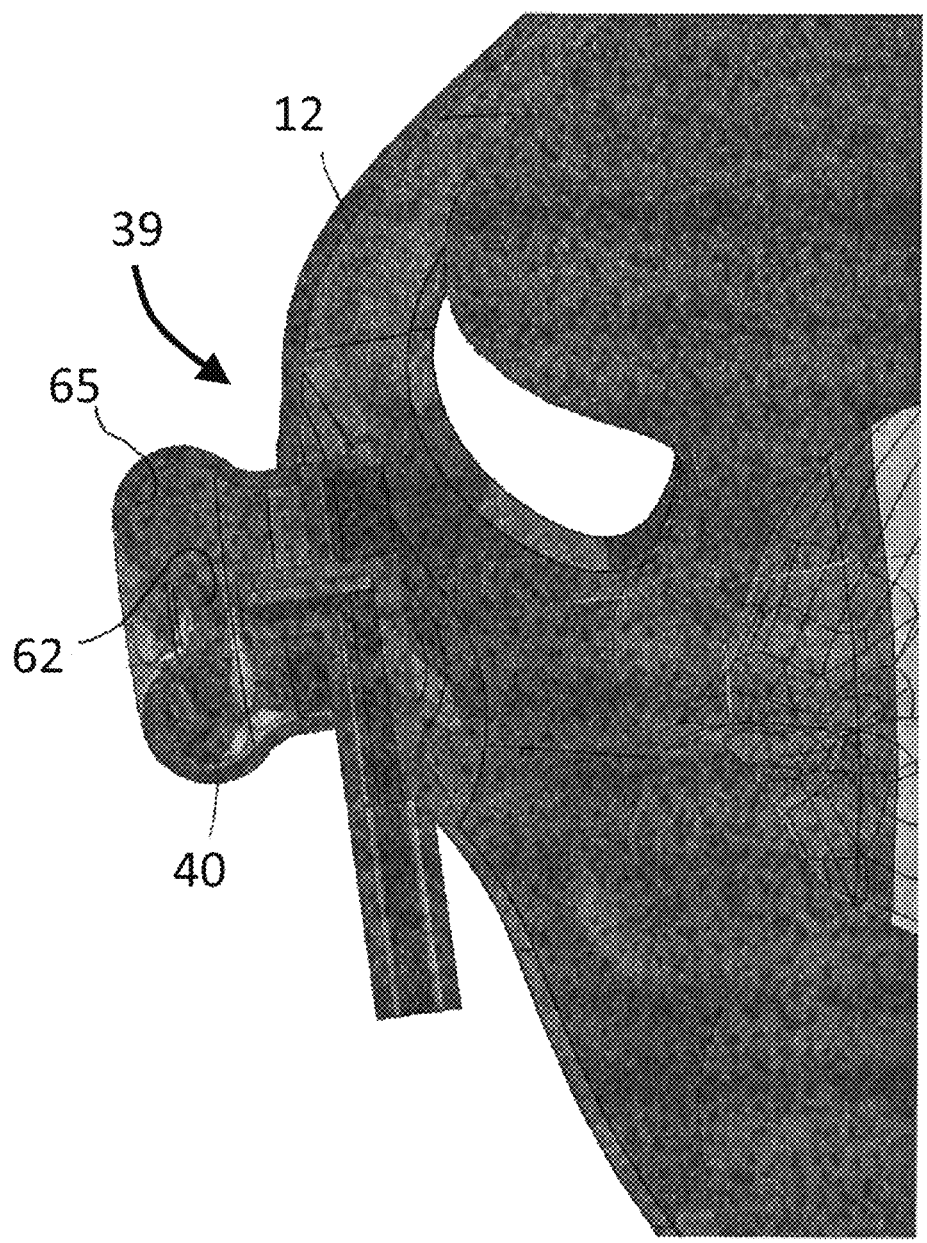
FIG. 8A is a sectional view as in FIG. 7A, in close up.

As seen in FIG. 5A, oxygen flow entering diffuser through inlet conduit follows an initial upward path, followed by a horizontal path within axial conduit, towards the discharge outlet 54 of axial tube 50. The discharged oxygen then enters rebound chamber, where the gas stream impacts central cone 62 which spreads the gas flow to evenly contact the curved wall of torus-shaped portion of diffuser chamber. The curved interior wall of this portion serves to redirect the oxygen flow in a reversal of flow direction, whereby the oxygen flow is directed rearwardly towards the user's face, through throat 66 and is discharged through outlet ports 68a-d. The gas flow is essentially laminar and non-turbulent within diffuser 40 until it funnels through outlet ports 68a-d and exits diffuser 40. Ports 68a-d may be configured to introduce turbulence into the gas stream and generate upper and lower turbulent gas plumes for enveloping the user's nose and mouth regions respectively, as seen in FIGS. 7A and 8A.

Figure 9A:
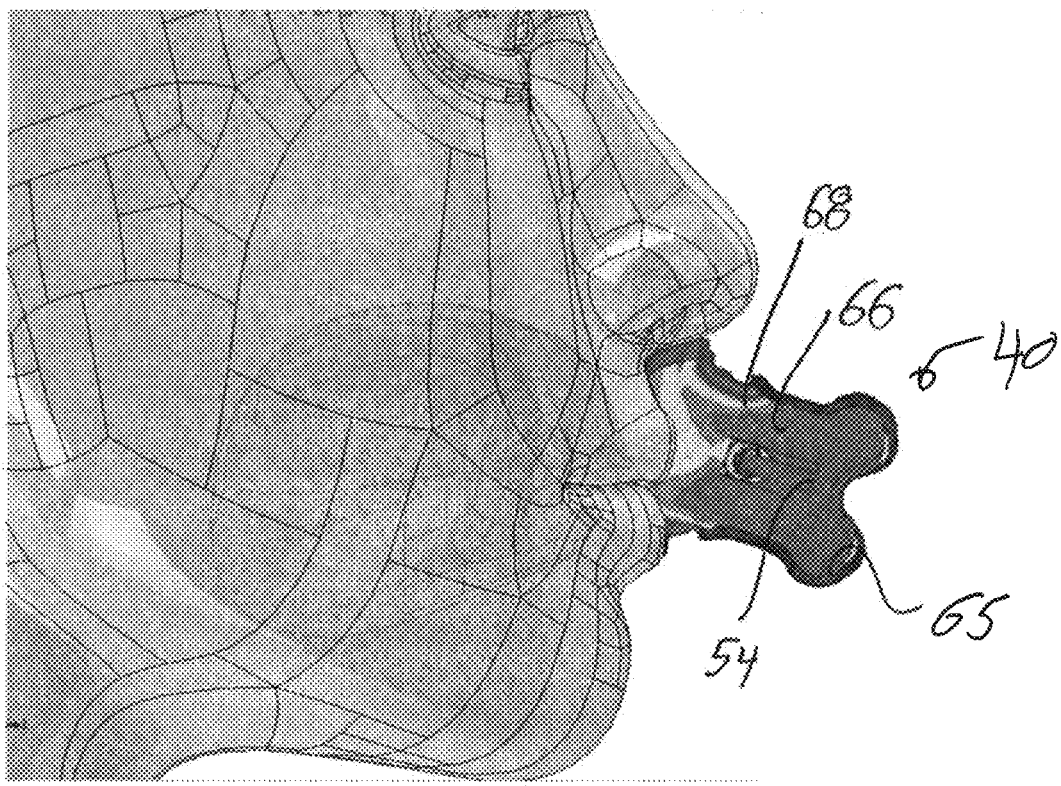
FIG. 9A is a flow simulation, showing simulated gas delivery concentrations when the present embodiment is in use with a patient.

As seen in FIGS. 6A-8A, mask 10 is configured to be worn so as to substantially cover the patient's nose and mouth, whereby diffuser 40 is positioned between the users nose and mouth. FIG. 9A is a gas flow simulation, which depicts oxygen flow to the user's nose and mouth from the upper and lower ports 68a-d.

As seen in FIG. 9A, diffuser 40 is generally centered over the user's mouth and positioned approximately 10 mm from this portion. When centered in this fashion, the upper and lower turbulent gas plumes are generally centered over the user's nose and mouth. The upper plume is deflected upwardly by the configuration of ports 68a and b to impact on the user's nostrils. Since diffuser 40 is centered below the user's nostrils, the upward deflection of the airflow from ports 68a and b tends to channel the airflow directly into the user's nostrils. Airflow from lower ports 68c and d exits diffuser 40 in an essentially straight path aligned with axis "a". Mask body 12 is configured to locate diffuser 40 such that lower ports 68c and d are approximately centered over the user's mouth. As such, airflow from lower port s 68c and d is directed directly towards the user's lips and mouth.

Figure 10A:
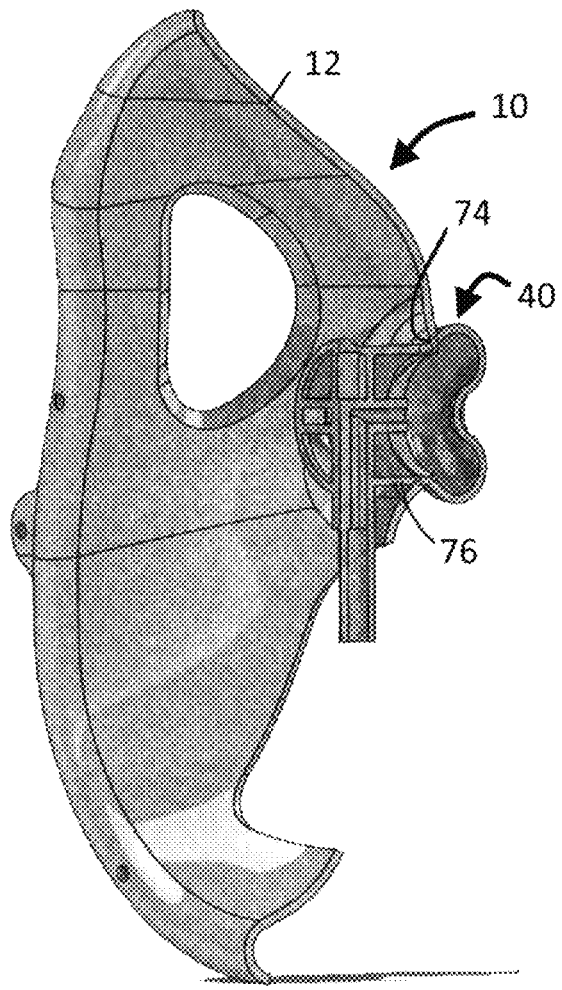
FIG. 10A is a side view of a further embodiment, in a retracted position.
Figure 11A:
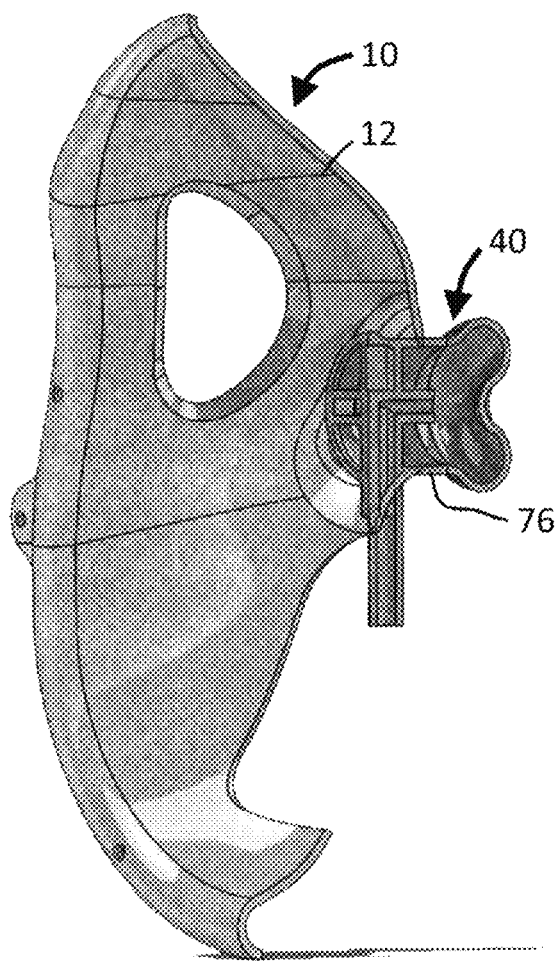
FIG. 11A is a side view as in FIG. 10A, in an extended position.

FIGS. 10A and 11A show a further embodiment in which diffuser 40 is slideably displaceable along horizontal axis "a" within diffuser assembly 72. According to this example, diffuser assembly 72 provides a circular opening 74 into the interior of mask body 12, which slideably engages cylindrical wall 76 of diffuser 40. Diffuser may be displaced between a rearward, first position shown in FIG. 10A and a forward, second position seen in FIG. 11, as well as any position between these limits. This function permits an adjustment of the gap between diffuser 40 and the user's face to accommodate the user's facial structure and/or to fine-tune gas delivery for user comfort.

Figure 12A:
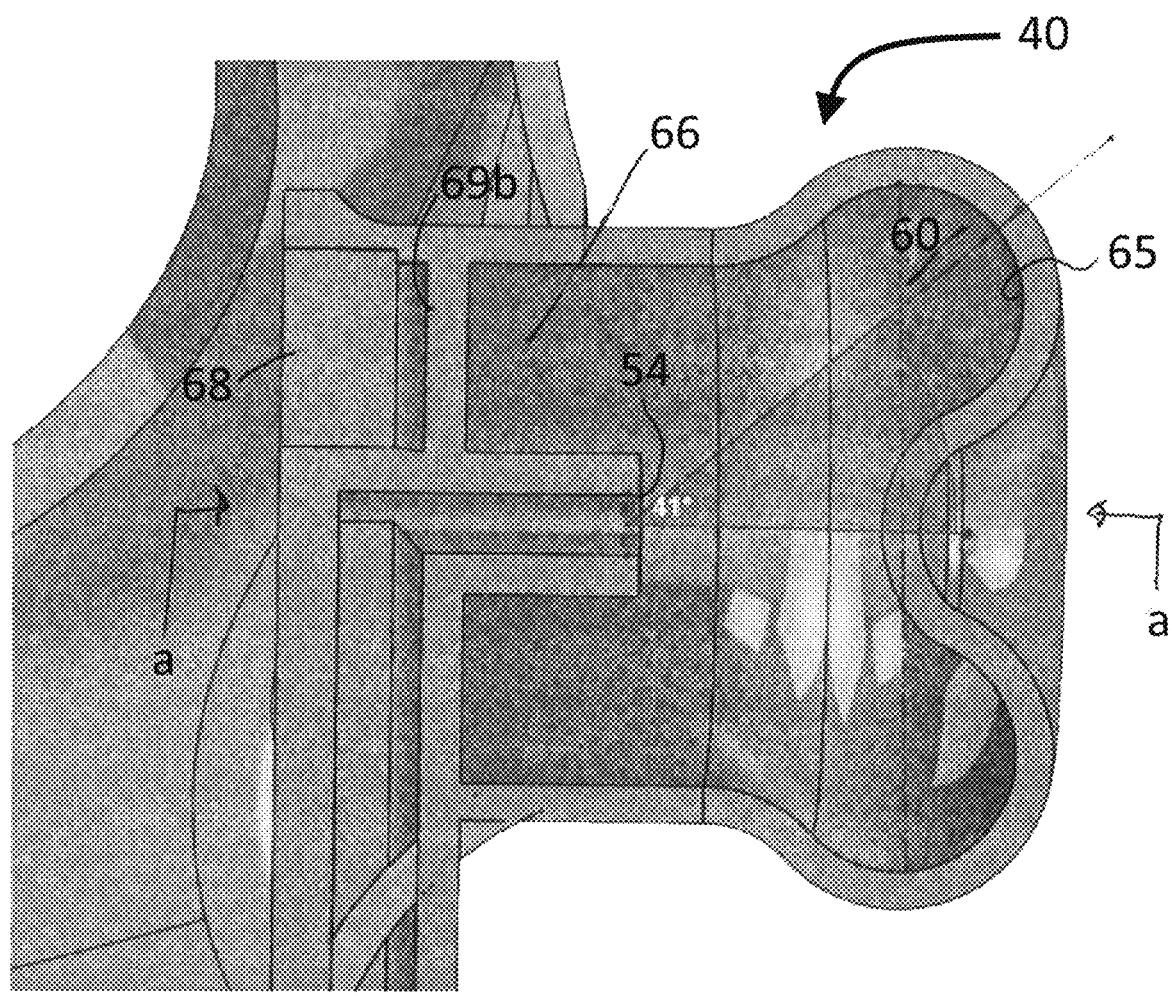
FIG. 12A is a cross-sectional view of the diffuser, showing internal angular dimensions.
Figure 13A:
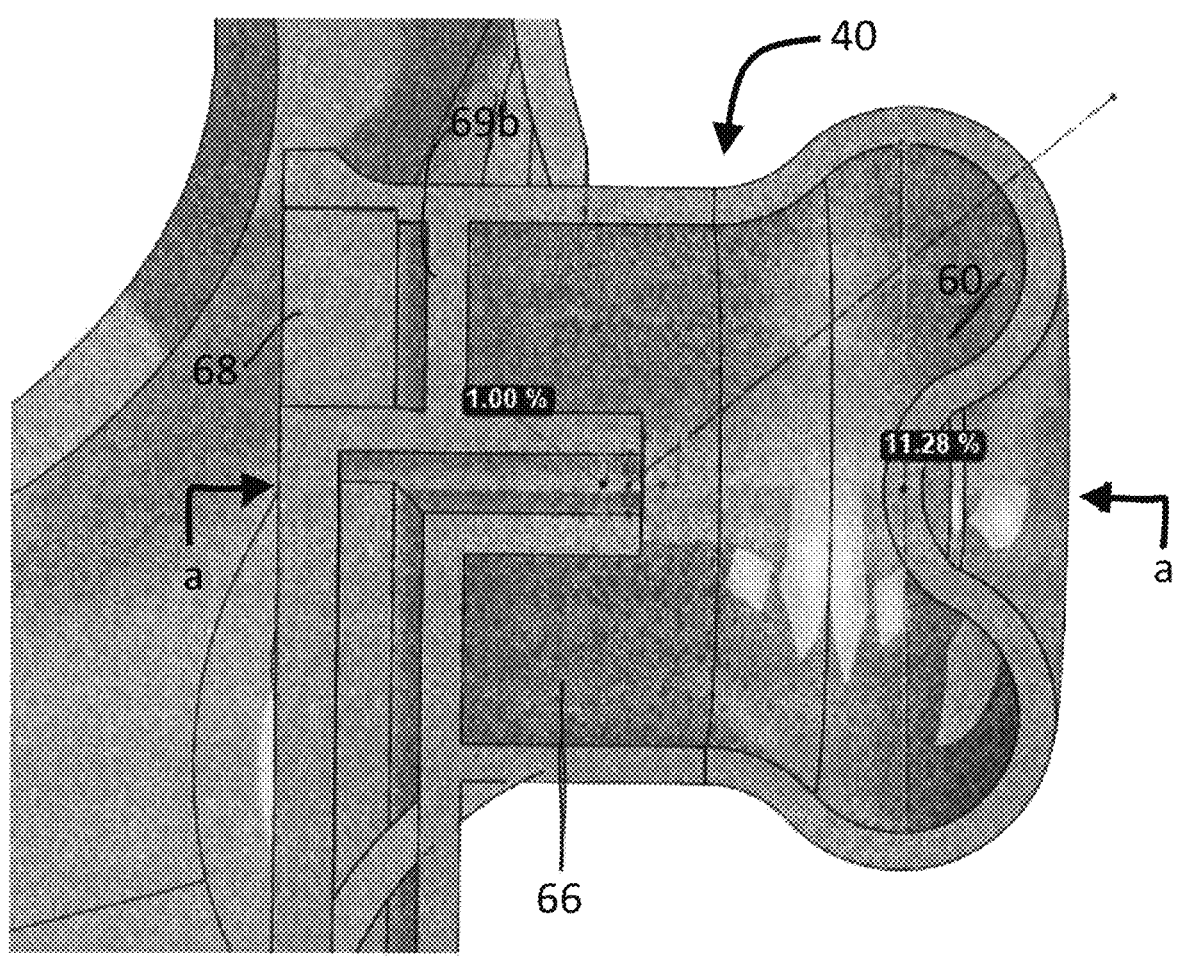
FIG. 13A is a cross-sectional view as in FIG. 12A, showing additional dimensions.

FIGS. 12A and 13A show certain internal dimensions of diffuser 40. As seen in FIG. 12A, the configuration of rebound chamber 60 may be expressed as an angular displacement of a point on surface 65 which is maximally displaced from the center of mouth 54, relative to axis "a". In one example, this angular displacement is 41°. In other examples, this angular displacement is in the range of about 30° to about 60°.

As seen in FIG. 13A, gas rebound chamber 60 has a maximum internal diameter x and mouth 54 has an internal diameter y. In one example, the ratio of x:y is approximately 11:1. In other examples, this ratio can range from about 5:1 to about 15:1. The internal diameter y in one example ranges from about 2 to about 10 mm.

Figures 14A, 15A:
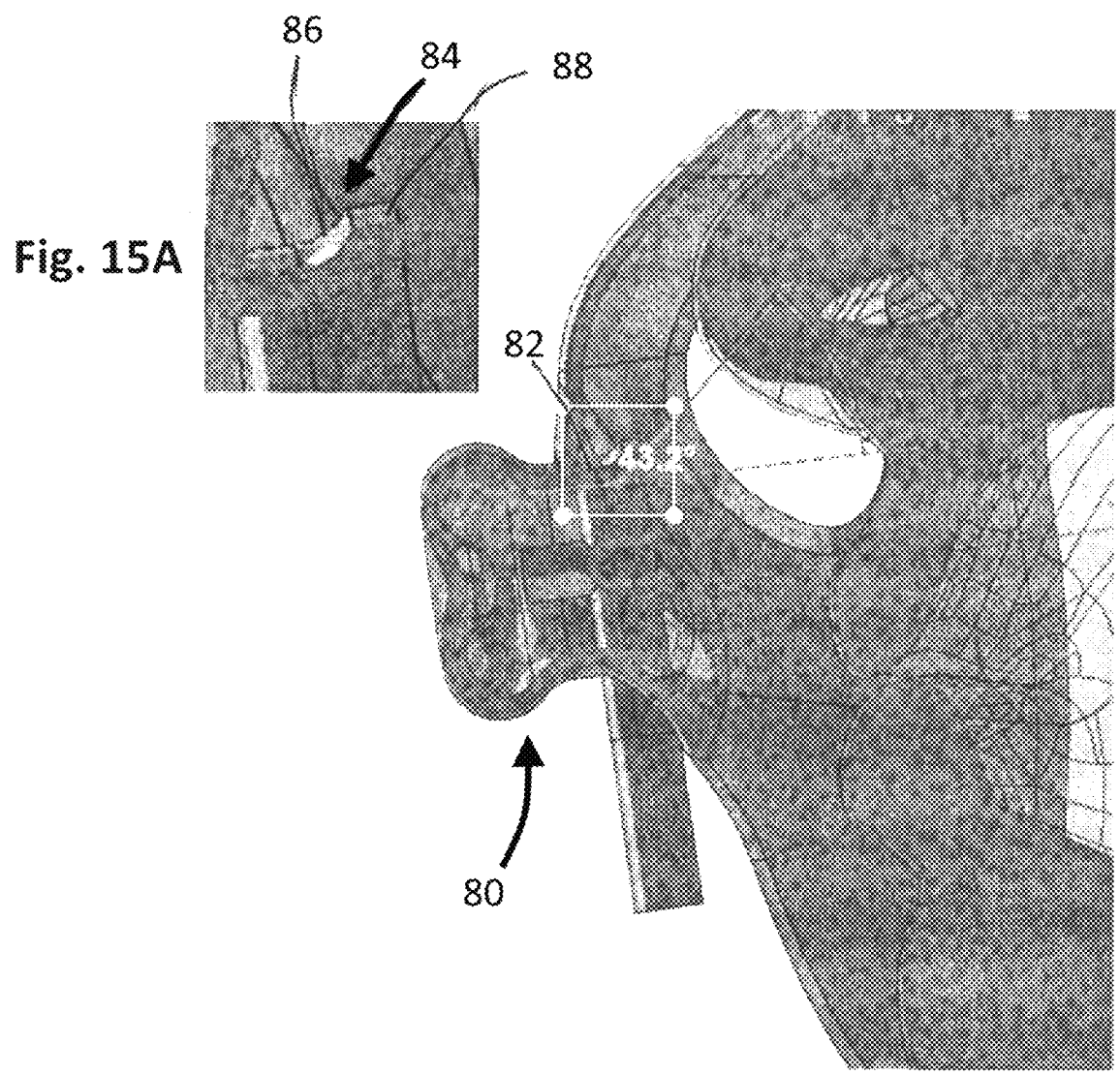
FIG. 14A is a cross-sectional view of a further embodiment of the mask, showing the mask in use on a patient.
FIG. 15A is an enlarged view of a portion of FIG. 14A within the area shown within the box in FIG. 14A.

FIGS. 14A and 15A show a further embodiment of a diffuser 80, having a configuration similar to preceding diffuser 40. Diffuser 80 is characterized by its gas discharge end in which a throat 82 is provided that has a rearward-facing, bell-shaped lip 84 at its outlet, facing the user. Lip 84 comprises a conical segment 86 which tapers outwardly and rearwardly from throat 82, merging with a rim 88 which forms the exposed rearward edge of diffuser 80. As seen in detail in FIG. 15, rim 88 is approximately parallel to and co-axial with the wall of throat 82, whereby lip 84 forms an approximately S-shaped configuration when seen in cross-section.

As seen in FIG. 14A, in one example, lip 84 defines an angle of 43.2° between axis "a" and the straight line which contacts the exposed inner edge of rim 88. It will be seen that this angle of lip 84 affects the dimensions of the plume generated by diffuser 80.

Figure 16A:
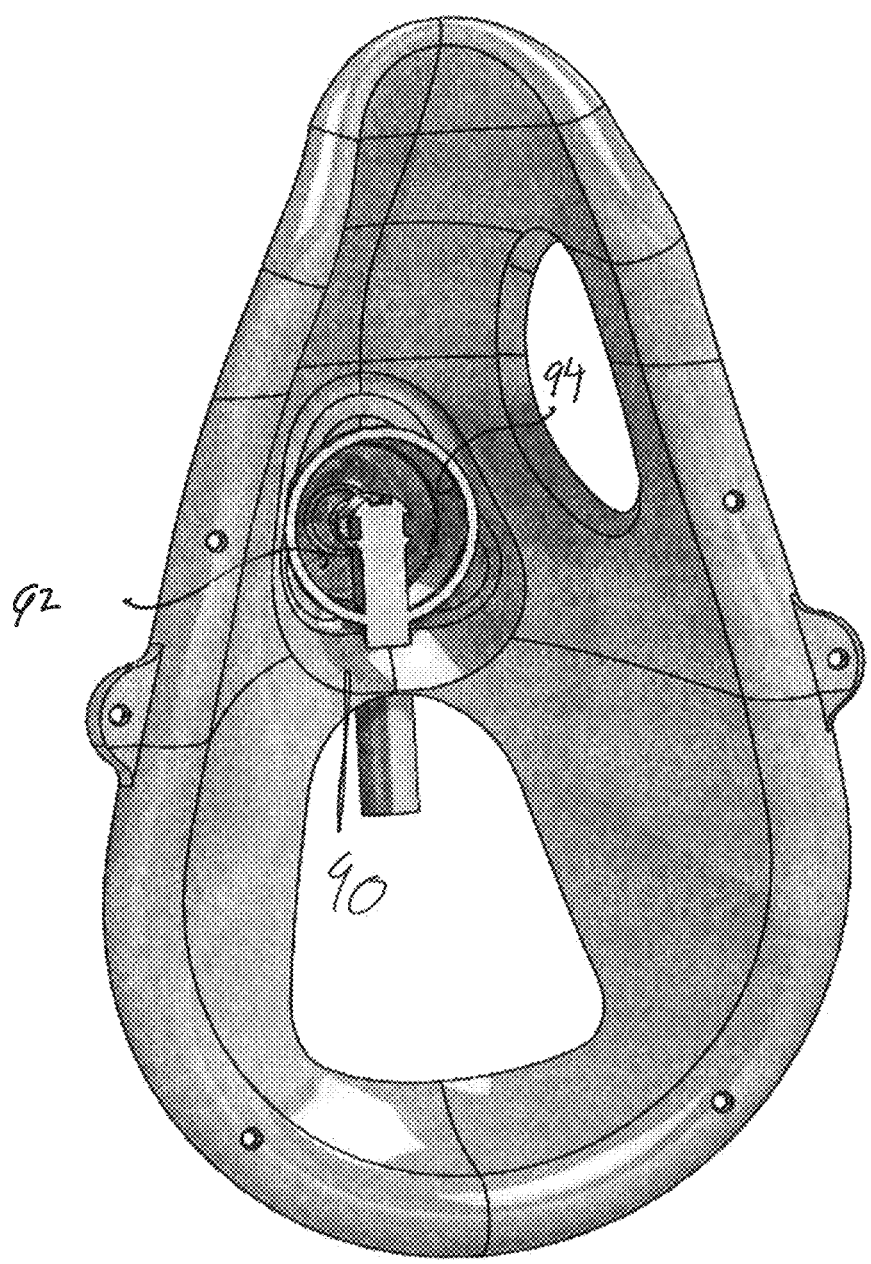
FIG. 16A is a perspective view, from the rear, of a further embodiment of the mask.

FIG. 16A shows a further embodiment, in which diffuser 90 is similar in structure to preceding diffuser 40 described above. According to this example, diffuser 90 is characterized by a throat 92 having an annular outlet 94 which is unobstructed by the septums and barrier walls of the outlet of the preceding diffuser 40. As such, outlet 94 is obstructed only by a portion of inlet conduit 96, which extends radially inwardly towards the axis of throat 92. Throat 92 has an annular configuration around axial inlet conduit 96, which is similar in structure to diffuser 40.

FIGS. 17A-19A show a further embodiment of a diffuser assembly 1100, in which the mask body omitted from the drawings in order to more clearly show the structure of diffuser assembly 1100. However, it will be understood that diffuser assembly 1100 is normally integrated within a mask body in a similar fashion as the preceding examples. Diffuser assembly 1100 comprises three separate individual diffusers, consisting of a lower diffuser 1102, which is centrally located and left and right upper diffusers 104 and 106. When installed in a mask body, lower diffuser 1102 is approximately directly opposed to a user's mouth. Left and right upper diffusers 104 and 106 are located above lower diffuser 1102, and normally oppose a user's nose when installed in a mask that is worn by a patient. Diffusers 1102, 104 and 106 thus define three corners of an inverted triangle. Diffusers 1102, 104 and 106 are joined together by a gas conduit structure 108, which retains the diffusers in a spaced apart, triangular configuration and distributes gas flow to the three diffusers, as discussed below. Gas conduit structure comprises a vertical, central gas conduit 1110, which has a central inlet 1112 for connection to an external gas tube, not shown. Branch conduits 1114 and 1116 extend from the upper end of central conduit 1110 and lead to the respective left and right upper diffusers 104 and 106. The respective conduits 1110, 1114 and 1116 internally communicate to distribute gas through to all of the respective diffusers.

Lower diffuser 1102 has a similar configuration to diffuser 40 of the preceding embodiment, although scaled-down. As such, diffuser 1102 comprises a gas rebound chamber 1120, a narrowed, annular throat 122 and an outlet port 1124. However, outlet port 1124 is not internally divided with septums, but instead comprises an annular opening the directly discharges air from throat 122 without dividing the airflow into separate streams.

Upper diffusers 104 and 106 are scaled down still further from lower diffuser 1102 and have essentially the same configuration. Upper diffusers 104 and 106 are oriented to discharge air directly to the patient's nostrils, whereby the spacing and orientation of the respective diffusers is configured to direct two separate airstreams at the patient's respective nostrils.

A further embodiment is shown in FIGS. 20A-22A. According to this example, a mask body 202 is provided with an open structure similar to the mask of the preceding examples comprising a large openings in mask body 202 to provide easy access to the patient's face. Mask 200 is shown in this example with additional bridges 18 and open areas 20, to provide an even more open structure than the preceding examples. It will be understood that the mask configuration of this embodiment may also be used with the preceding embodiments, with minor structural modifications. Mask body 202 has a diffuser retainer 204 comprising a wall that projects inwardly from central hub 206. Mask body 202 further comprises internal ribs 208 that projecting rearwardly from the inside surfaces of bridges 18, and radiate outwardly from retainer 204. Retainer 204 comprises a wall protruding rearwardly towards the user, which encircles a space for receiving a diffuser 210. Retainer 204 is shown with a triangular configuration, although other configurations may be used.

Diffuser 210 comprises a triangular side wall 212 configured to fit within retainer 204 and be secured therein, for example by friction fit and optionally an adhesive, melt-welding or other attachment means. Side wall 212 has an inside surface 213 facing the interior of diffuser 210, and which may be tapered outwardly and rearwardly. The forward end of diffuser 210 is sealed with a dome 214, which comprises a sloping, tapered region 216 extending forwardly from side wall 212, and a flat end wall 1218. Dome 214 is thus configured as a frustoconical (truncated cone). Tapered region 216 surrounds flat end wall 1218 and projects it forwardly from side wall 212, to form a dome-shaped interior space in which the forwardmost surface is formed by the inside surface of flat end wall 1218. The opposing rear end 1220 of diffuser 210 facing the user is open, to permit airflow to the user.

Figure 21:
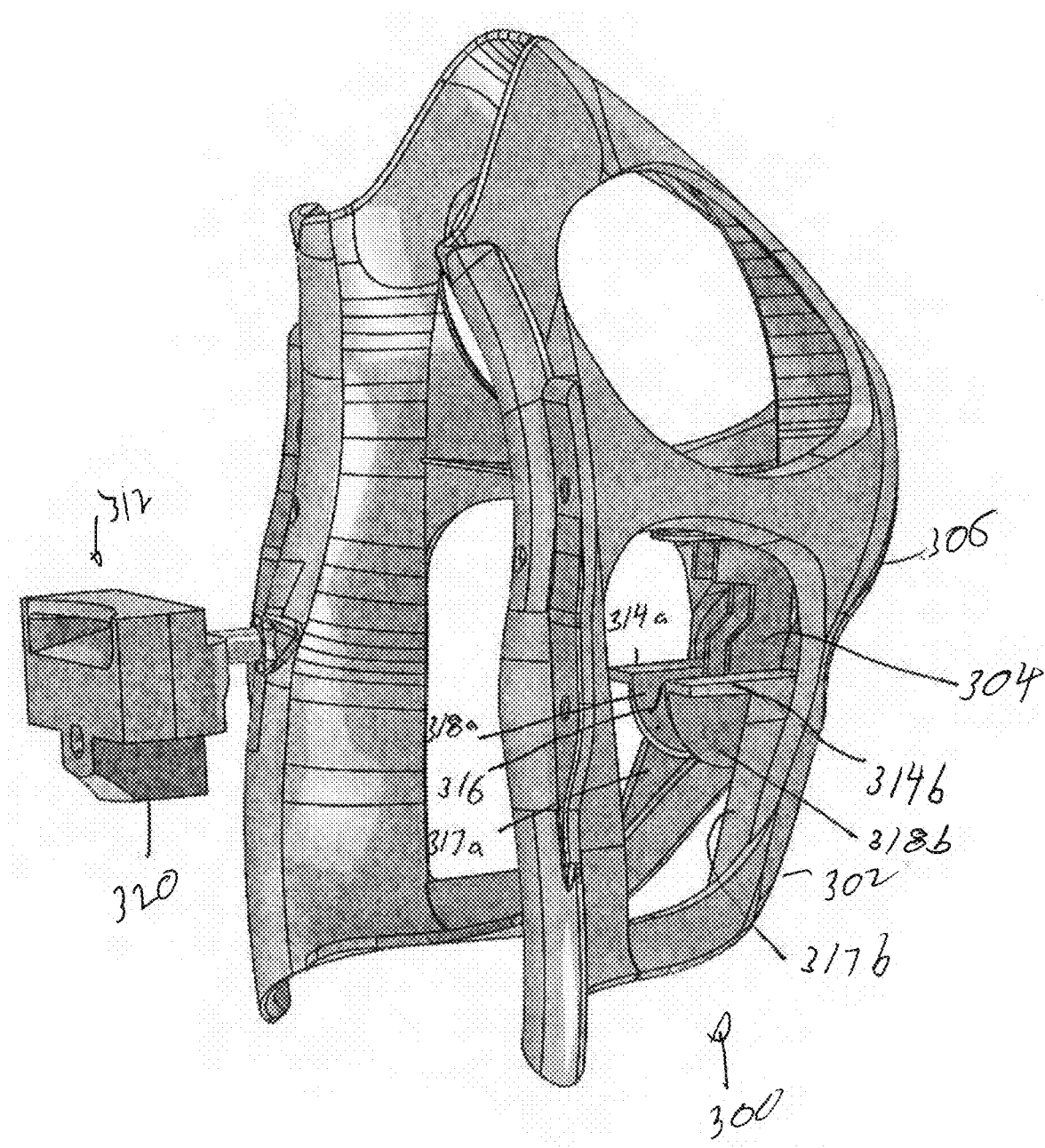
FIG. 21 is a perspective, exploded view of a further embodiment having a slideable diffuser.
Figure 21A:
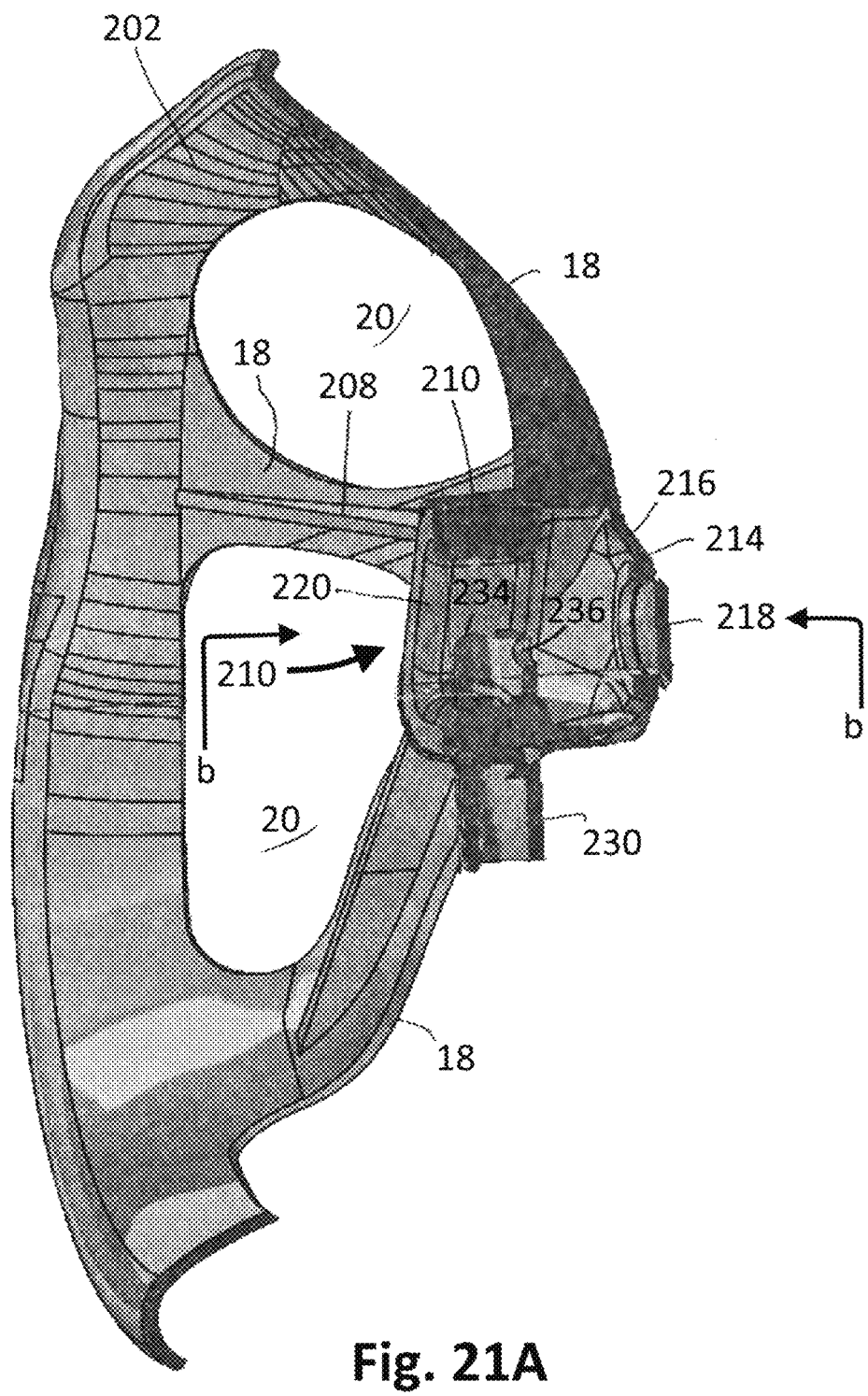
FIG. 21A is a cross-sectional view of the embodiment of FIG. 20A.
Figure 23:
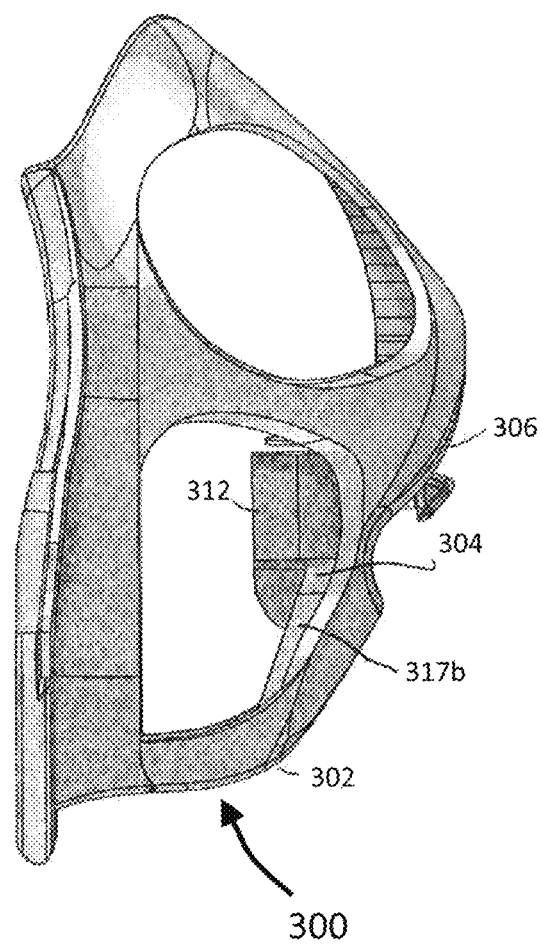
FIG. 23 is a side elevational view thereof, with the diffuser in the retracted position.

For reference, a central axis "b" extends longitudinally between flat end wall 1218 and rear end 1220 (see FIG. 21A).

Diffuser 210 further comprises a vertical gas inlet tube 1230, having a central bore 232. Tube 1230 terminates at its lower end in an inlet for connection to a gas supply tube, not shown. An upper portion 231 of gas tube 1230 projects into the interior of diffuser 210, and a lower portion thereof projects downwardly from diffuser 210. The uppermost end of tube 1230 is sealed by top cap 234. Tube 1230 discharges gas through a gas nozzle 236, which opens to a lateral side of tube 1230 adjacent to top cap 234. Nozzle 236 is co-axial with central axis "b" and is configured to discharge a stream of gas forwardly towards flat end wall 1218, in a direction aligned with axis "b".

Figure 22:
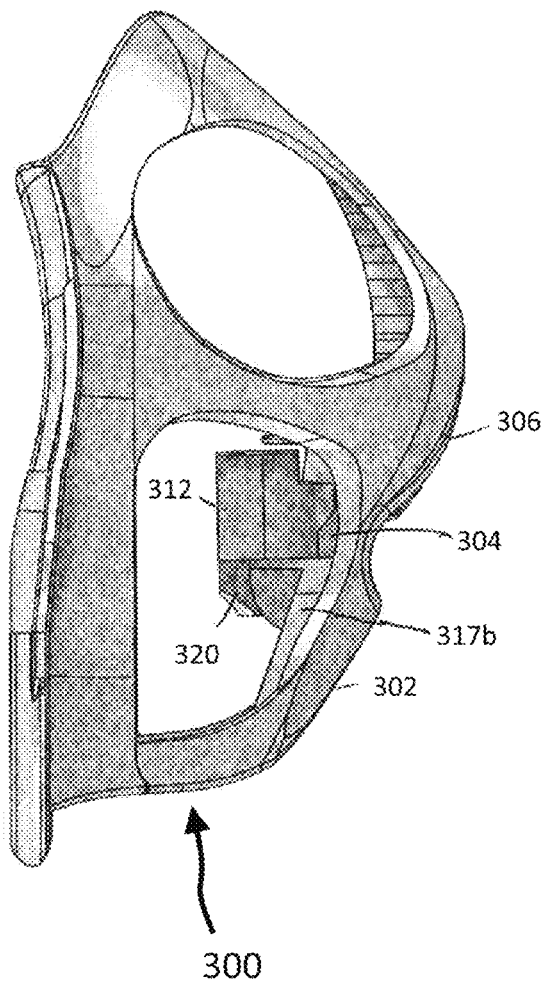
FIG. 22 is a side elevational view thereof, with the diffuser in the extended position.
Figure 22A:
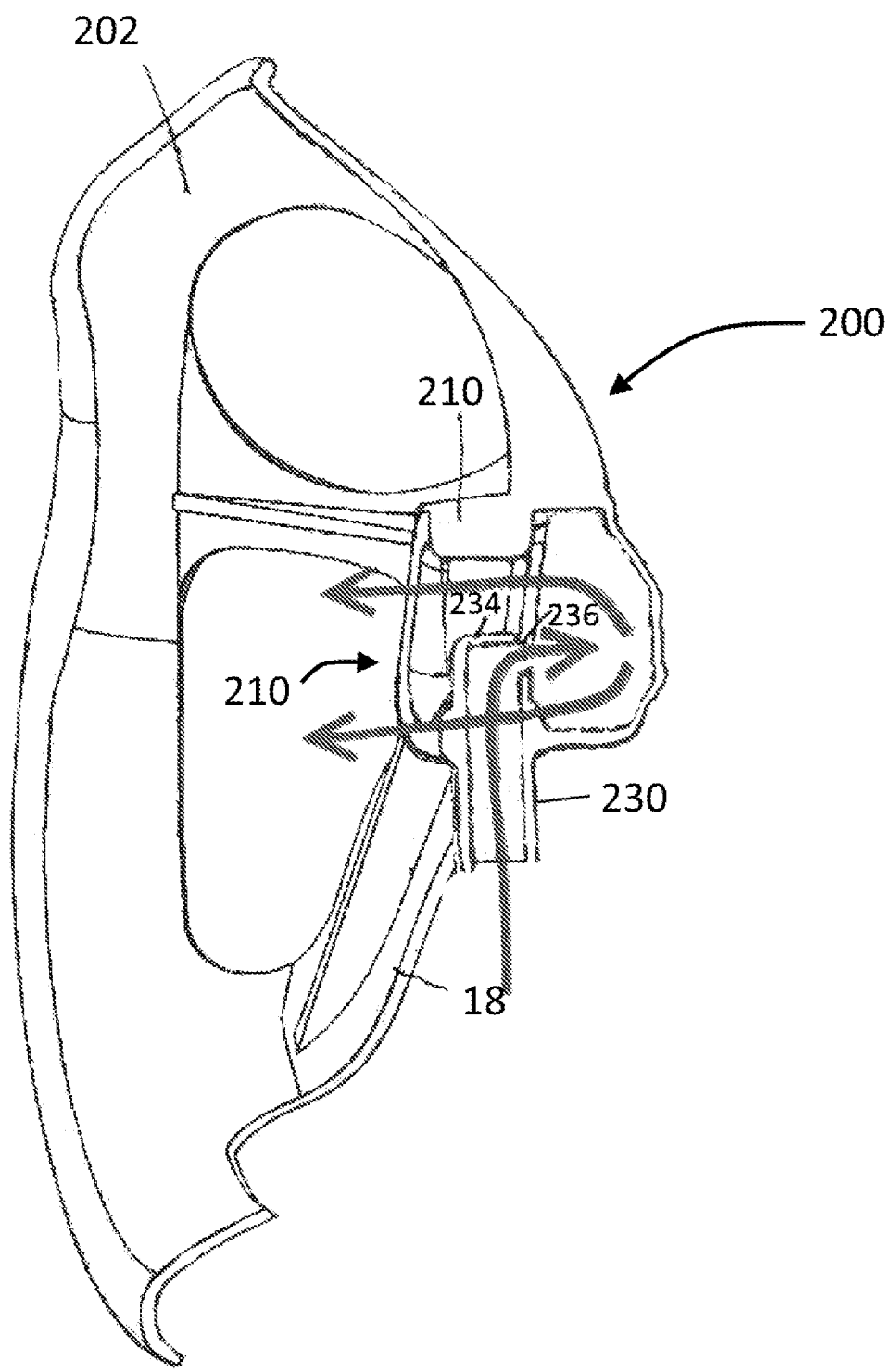
FIG. 22A is a cross-sectional view as in FIG. 21A, showing internal gas flow.
Figure 24:
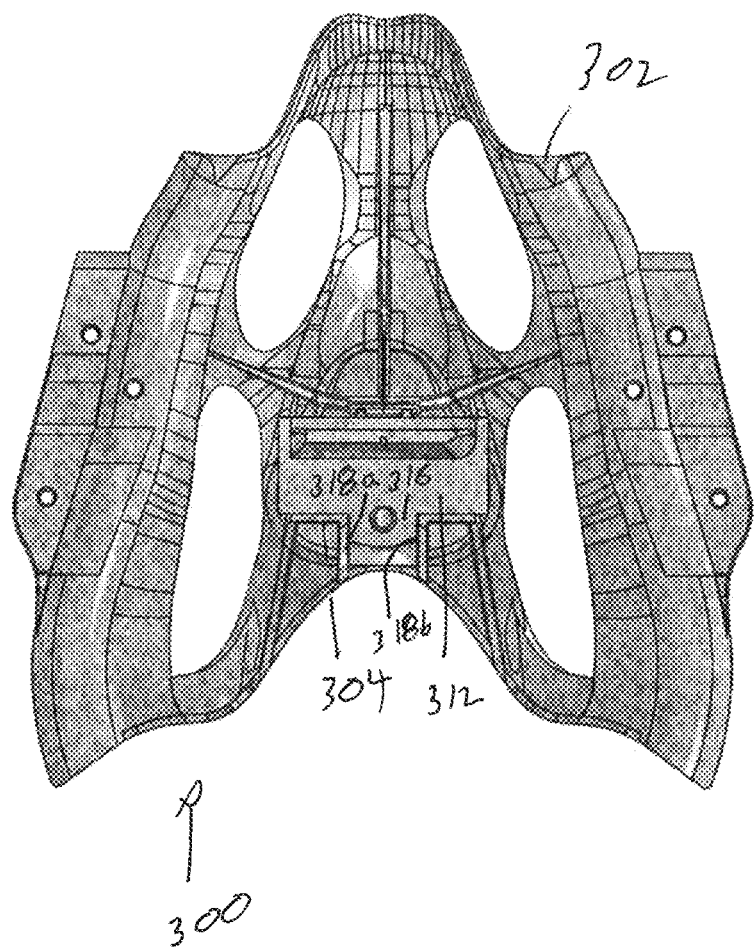
FIG. 24 is a rear elevational view thereof.

As seen in FIG. 22A, a gas stream exits nozzle 236 in a forward direction and impacts the inside surface of flat end wall 1218. The inside surface of dome 214 forms a gas rebound chamber which redirects the gas flow rearwardly, whereupon it is discharged through rear end 1220 towards the patient's face. The interior surface of dome 214 is configured to rebound gas flow exiting from nozzle 236 to generate a similar gas flow pattern as the preceding examples.

It will be seen that in the present example of the invention, gas flow through diffuser 210 is not divided into discrete upper and lower streams as it exits diffuser 210 as in the first embodiment described above, but is instead discharged in a single stream towards the user. The gas flow discharged towards the user tends to form a turbulent plume over the user's nose and mouth, and which is substantially confined within the interior of mask body 202.

The embodiments described above are intended to provide representative examples of the invention. Alterations, modifications and variations may be made to these embodiments without departing from the intended scope of the invention. The scope of the invention should not be limited by the preferred embodiments set forth in the examples but should be given the broadest interpretation consistent with the specification as a whole. The claims are not to be limited to the preferred or exemplified embodiments of the invention.

The invention claimed is:

1. A mask for administering a breathable gas to a patient comprising a mask body configured to cover the nose and mouth of a patient and a diffuser mounted to the mask body for diffusing the gas rearwardly to the nose and mouth of the patient, the mask body configured to position the diffuser spaced from and opposing a nose and mouth region of the patient, the diffuser comprising:

a diffuser body;

a bore within the diffuser body, terminating at one end in a gas inlet for connection to a gas source;

a first nozzle within the diffuser body, communicating with the bore to direct a first portion of gas flow rearwardly in a first plume configured to direct the first portion of gas to the patient's mouth; and a second nozzle within the diffuser body, communicating with the bore to direct a second portion of gas flow rearwardly in a second plume directed towards the patient's nostrils;

wherein the first and second nozzles are configured whereby the first plume is more narrowly focused than the second plume.

2. The mask of claim 1 wherein the first nozzle comprises a conical bore that diverges outwardly and rearwardly towards the patient's mouth.

3. The mask of claim 1 wherein the second nozzle comprises a slot having an elongate axis that is generally horizontal when the mask is upright, the slot comprising a mouth that opens rearwardly towards the patient.

4. The mask of claim 1 wherein the diffuser body further comprises a gas flow deflector projecting rearwardly towards the user from the second nozzle and configured to shape the gas plume from the second nozzle upwardly towards the patient's nostrils.

5. The mask of claim 1 wherein the first nozzle is configured whereby the first plume is directed substantially horizontally and the second nozzle is configured whereby the second plume is directed rearwardly and upwardly to impact on the patient's nostrils.

6. The mask of claim 1 wherein the mask body comprises a retainer configured to retain the diffuser to the mask body, whereby the diffuser body is slideably retained to the mask body for sliding along a linear path to selectively increase or decrease the space between the patient's face and the diffuser.

7. The mask of claim 1 wherein the diffuser further comprises an inlet configured to receive exhaled breath from the patient, said inlet being in fluid communication with an internal bore for connection to a gas conduit.

8. The mask of claim 1 wherein the diffuser comprises a valve assembly for selectively channeling incoming gas solely to the first nozzle or to a combination of the first and second nozzles.

9. A mask for administering a breathable gas to a patient comprising a mask body configured to cover the nose and mouth of a patient and a diffuser for diffusing the gas rearwardly to the nose and mouth of the patient, the mask body configured to position the diffuser spaced from and opposing a nose and mouth region of the patient, the diffuser comprising a diffuser body; wherein the mask body comprises a retainer that is configured to retain the diffuser to the mask body, whereby the diffuser body is slideably retained to the mask by the retainer wall for sliding along a linear path to selectively increase or decrease the space between the patient's face and the diffuser.

10. A mask for administering a breathable gas to a patient comprising a mask body configured to cover the nose and mouth of a patient and a diffuser mounted to the mask body for diffusing the gas to the nose and mouth of the patient, the mask body configured to position the diffuser spaced from and opposing a nose and mouth region of the patient, the diffuser comprising:

a diffuser body a gas conduit at least partially housed within the diffuser body and comprising an inlet for connection to a gas source and a conduit outlet within the interior of the diffuser body, the outlet being configured to discharge a stream of gas into the interior of the diffuser body in a forward direction away from the patient's face;

a rebound chamber within the diffuser body having a rebound surface spaced apart from and opposed to the gas conduit outlet, the rebound surface being configured to rebound and reverse the direction of flow of at least a substantial portion of the gas stream exiting the conduit outlet from the forward direction to a rearward direction towards the patient's face; and at least one diffuser outlet in fluid communication with the rebound chamber for channeling the gas stream from the rebound chamber towards the patient's face.

11. The mask of claim 10 wherein the gas conduit comprises a first segment which is generally vertical, a second segment which is generally horizontal and an elbow connecting the first and second segments, wherein the inlet comprises an end of the first segment and the outlet comprises an end of the second segment.

12. The mask of claim 10 wherein the rebound surface has a curved surface around its perimeter, which is configured to redirect the gas stream in a curving path from the direction away from the patient's face to the direction towards the patient's face.

13. The mask of claim 10 wherein the diffuser outlet comprises multiple ports, comprising at least one upper port configured to direct a portion of the gas stream to the patient's nostrils and at least one lower port configured to direct a portion of the gas stream to the patient's mouth.

14. The mask of claim 10 comprising multiples ones of said diffuser, said diffusers being joined by a connection structure configured to position the diffusers over the patient's mouth and nose respectively.

15. The mask of claim 10 wherein the rebound chamber further comprises a gas flow spreader comprising a member opposed to and projecting towards the gas conduit outlet and configured to spread the gas stream prior to contacting the rebound surface.

16. A diffuser for a mask for administering a breathable gas to a patient, the diffuser comprising:

a diffuser body;

a gas conduit at least partially housed within the diffuser body and comprising an inlet for connection to a gas source and a gas conduit outlet within the interior of the diffuser body, the gas conduit outlet being configured to discharge a stream of gas into the interior of the diffuser body in a forward direction away from the patient's face;

a rebound chamber within the diffuser body having a rebound surface spaced apart from and opposed to the gas conduit outlet, the rebound surface being configured to rebound and reverse the direction of flow of at least a substantial portion of the gas stream exiting the gas conduit outlet from the forward direction to a rearward direction towards the patient's face; and at least one diffuser outlet in fluid communication with the rebound chamber for channeling the gas stream from the rebound chamber towards the patient's face.

17. The diffuser of claim 16 wherein the gas conduit comprises a first segment which is generally vertical, a second segment which is generally horizontal and an elbow connecting the first and second segments, wherein the inlet comprises an end of the first segment and the outlet comprises an end of the second segment.

18. The diffuser of claim 16 wherein the rebound chamber comprises a gas flow spreader comprising a member opposed to and projecting towards the gas conduit outlet and configured to spread the gas stream prior to contacting the rebound surface.

19. The diffuser of claim 16 wherein the rebound surface has a curved surface around its perimeter, which is configured to redirect the gas stream in a curving path from the direction away from the patient's face to the direction towards the patient's face.

20. The diffuser of claim 16 wherein the diffuser outlet comprises multiple ports, comprising at least one upper port configured to direct a portion of the gas stream to the patient's nostrils and at least one lower port configured to direct a portion of the gas stream to the patient's mouth.

21. The diffuser of claim 16 comprising multiples ones of said diffuser, said diffusers being joined by a connection structure configured to position the diffusers over the patient's mouth and nose respectively.

* * * * *